(12) United States Patent
Hirai et al.

(10) Patent No.: US 9,879,034 B2
(45) Date of Patent: Jan. 30, 2018

(54) NEAR-INFRARED ABSORPTION COMPOSITION, CURED FILM, NEAR-INFRARED CUT FILTER, SOLID-STATE IMAGING DEVICE, INFRARED SENSOR, AND COMPOUND

(71) Applicant: FUJIFILM Corporation, Tokyo (JP)

(72) Inventors: Yuki Hirai, Haibara-gun (JP); Daisuke Sasaki, Haibara-gun (JP); Yoshihiro Jimbo, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/677,538

(22) Filed: Aug. 15, 2017

(65) Prior Publication Data

US 2017/0342091 A1 Nov. 30, 2017

Related U.S. Application Data

(63) Continuation of application No. PCT/JP2016/055363, filed on Feb. 24, 2016.

(30) Foreign Application Priority Data

Feb. 26, 2015 (JP) .................. 2015-036778

(51) Int. Cl.
*C07D 521/00* (2006.01)
*C07F 5/02* (2006.01)

(52) U.S. Cl.
CPC ............ *C07F 5/022* (2013.01); *C07D 521/00* (2013.01)

(58) Field of Classification Search
CPC .............................. C07D 521/00; C07F 5/022
See application file for complete search history.

(56) References Cited

U.S. PATENT DOCUMENTS

| 2009/0227793 A1 | 9/2009 | Tian et al. |
| 2011/0245538 A1 | 10/2011 | Kato et al. |
| 2015/0260889 A1* | 9/2015 | Shiono ................. C08K 5/3417 252/587 |

FOREIGN PATENT DOCUMENTS

| JP | 10-36695 A | 2/1998 |
| JP | 2000-159776 A | 6/2000 |
| JP | 2008-298820 A | 12/2008 |
| JP | 23009-209297 A | 9/2009 |
| JP | 2011-208101 A | 10/2011 |
| WO | WO 2014/088063 A1 | 6/2014 |

OTHER PUBLICATIONS

International Search Report and Written Opinion of the International Searching Authority (Forms PCT/ISA/220, PCT/ISA/237 and PCT/ISA/210), dated Apr. 12, 2016, for International Application No. PCT/JP2016/055363, with an English translation.

* cited by examiner

*Primary Examiner* — Erich A Leeser
(74) *Attorney, Agent, or Firm* — Birch, Stewart, Kolasch & Birch, LLP

(57) ABSTRACT

To provide a near-infrared absorption composition which contains a squarylium compound having excellent solvent solubility, a cured film which uses the near-infrared absorption composition, a near-infrared cut filter, a solid-state imaging device, an infrared sensor, and a compound. A near-infrared absorption composition includes a compound represented by the following Formula (1) and a resin. $R^1$ and $R^2$ each independently represent "—$S^1$-$L^1$-$T^1$" or the like, $R^3$ and $R^4$ each independently represent a hydrogen atom or an alkyl group, $X^1$ and $X^2$ each independently represent an oxygen atom or —$N(R^5)$—, $R^5$ represents a hydrogen atom or the like, $Y^1$ to $Y^4$ each independently represent a substituent, p and s each independently represent an integer of 0 to 3, and q and r each independently represent an integer of 0 to 2; and $S^1$ represents an arylene group or the like, $L^1$ represents an alkylene group or the like, and $T^1$ represents an alkyl group or the like.

(1)

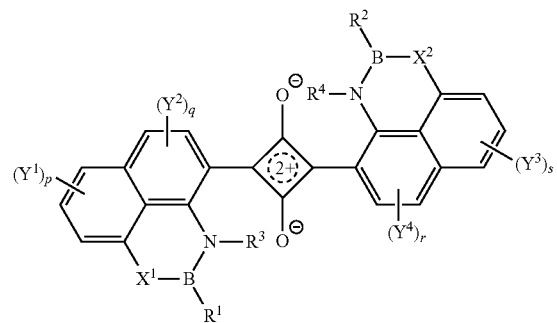

17 Claims, 1 Drawing Sheet

NEAR-INFRARED ABSORPTION COMPOSITION, CURED FILM, NEAR-INFRARED CUT FILTER, SOLID-STATE IMAGING DEVICE, INFRARED SENSOR, AND COMPOUND

CROSS-REFERENCE TO RELATED APPLICATIONS

This application is a Continuation of PCT International Application No. PCT/JP2016/055363 filed on Feb. 24, 2016, which claims priority under 35 U.S.C §119(a) to Japanese Patent Application No. 2015-036778 filed on Feb. 26, 2015. Each of the above application(s) is hereby expressly incorporated by reference, in its entirety, into the present application

BACKGROUND OF THE INVENTION

1. Field of the Invention

The present invention relates to a near-infrared absorption composition, a cured film, a near-infrared cut filter, a solid-state imaging device, an infrared sensor, and a compound.

2. Description of the Related Art

In a video camera, a digital still camera, a cellular phone with a camera function, or the like, a charge coupled device (CCD) or a complementary metal oxide semiconductor (CMOS) which is a solid-state imaging device for a color image is used. These solid-state imaging devices use a silicon photodiode having sensitivity to a near-infrared ray in a light receiving section thereof. Therefore, visibility correction is required and a near-infrared absorption filter is used in many cases.

As a near-infrared absorption substance, a squarylium compound or the like is known (for example, JP2011-208101A, JP2000-159776A, and JP2008-298820A).

SUMMARY OF THE INVENTION

The squarylium compound disclosed in JP2011-208101A is a compound which has absorption in an infrared region and is excellent in invisibility and robustness. The squarylium compound disclosed in JP2011-208101A is a compound which is low in solubility in a solvent, and is dispersed in a solvent to be used as a dispersion liquid.

From the viewpoint of simplification of a dispersion step and the like, it is desirable to develop a squarylium compound which is excellent in solubility in a solvent (also referred to as solvent solubility).

According to the examination of the inventors, it is found that the squarylium compound disclosed in JP2000-159776A and JP2008-298820A has low solvent solubility.

Accordingly, an object of the invention is to provide a near-infrared absorption composition which contains a squarylium compound having excellent solvent solubility, a cured film which uses the near-infrared absorption composition, a near-infrared cut filter, a solid-state imaging device, an infrared sensor, and a compound.

The inventors have conducted various examinations and, as a result, have found that a compound represented by Formula (1) to be described later has excellent solvent solubility, and completed the invention. The invention provides the followings.

<1> A near-infrared absorption composition comprising: a compound represented by Formula (1); and a resin,

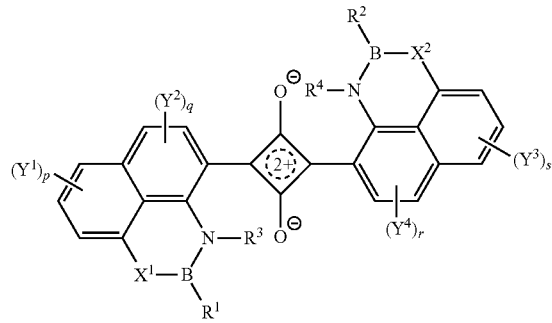

in the formula, $R^1$ and $R^2$ each independently represent an alkyl group, an alkenyl group, an aryl group, a heteroaryl group, or a group represented by Formula (W), at least one of $R^1$ or $R^2$ represents a group represented by Formula (W), $R^3$ and $R^4$ each independently represent a hydrogen atom or an alkyl group, $X^1$ and $X^2$ each independently represent an oxygen atom or $-N(R^5)-$, $R^5$ represents a hydrogen atom, an alkyl group, an aryl group, or a heteroaryl group, $Y^1$ to $Y^4$ each independently represent a substituent, each of $Y^1$ and $Y^2$, and $Y^3$ and $Y^4$ may be bonded to form a ring structure, in a case where the compound represented by Formula (1) has more than one of each of $Y^1$ to $Y^4$, these may be bonded to each other to form a ring structure, respectively, p and s each independently represent an integer of 0 to 3, and q and r each independently represent an integer of 0 to 2, and $$-S^1-L^1-T^1 \quad (W)$$

in Formula (W), $S^1$ represents a single bond, an arylene group, or a heteroarylene group, $L^1$ represents an alkylene group, an alkenylene group, an alkynylene group, $-O-$, $-S-$, $-NR^{L1}-$, $-CO-$, $-COO-$, $-OCO-$, $-CONR^{L1}-$, $-NR^{L1}CO-$, $-SO_2-$, $-OR^{L2}-$, or a group obtained by combining two or more thereof, $R^{L1}$ represents a hydrogen atom or an alkyl group, $R^{L2}$ represents an alkylene group, $T^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group, in a case where $S^1$ is a single bond, $L^1$ is an alkylene group, and $T^1$ is an alkyl group, the total number of carbon atoms included in $L^1$ and $T^1$ is not less than 13, and in a case where $S^1$ is an arylene group, the total number of carbon atoms included in L and $T^1$ is not less than 5.

<2> The near-infrared absorption composition according to <1>, in which in Formula (W), $S^1$ is an arylene group or a heteroarylene group.

<3> The near-infrared absorption composition according to <1> or <2>, in which in Formula (W), $L^1$ is an alkylene group, an alkenylene group, $-O-$, $-OR^{L2}-$, or a group obtained by combining two or more thereof, and $R^{L2}$ is an alkylene group.

<4> The near-infrared absorption composition according to any one of <1> to <3>, in which in Formula (W), a $-L^1-T^1$ portion includes a branched alkyl structure.

<5> The near-infrared absorption composition according to any one of <1> to <4>, in which in Formula (W), a -L$^1$-T$^1$ portion includes asymmetric carbon.

<6> The near-infrared absorption composition according to any one of <1> to <5>, in which the compound represented by Formula (1) includes two or more types of optical isomers.

<7> The near-infrared absorption composition according to any one of <1> to <6>, in which in Formula (1), R$^3$ and R$^4$ each independently represent a hydrogen atom or a methyl group.

<8> The near-infrared absorption composition according to any one of <1> to <7>, in which in Formula (1), p, q, r, and s are 0.

<9> The near-infrared absorption composition according to any one of <1> to <8>, in which in Formula (1), X$^1$ and X$^2$ are oxygen atoms.

<10> The near-infrared absorption composition according to any one of <1> to <8>, in which in Formula (1), X$^1$ and X$^2$ each independently represent any one of the followings:

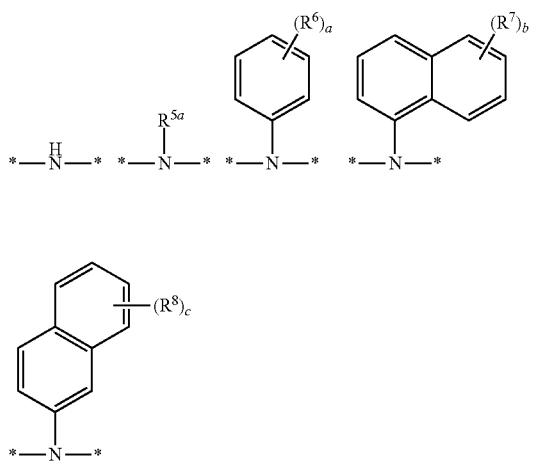

in the formula, R$^{5a}$ represents an alkyl group, R$^6$ to R$^8$ each independently represent a substituent, a represents an integer of 0 to 5, b and c each represent an integer of 0 to 7, and * represents a bond.

<11> The near-infrared absorption composition according to any one of <1> to <10>, further comprising: a solvent.

<12> The near-infrared absorption composition according to any one of <1> to <11>, further comprising: a curable compound.

<13> A cured film which is prepared using the near-infrared absorption composition according to any one of <1> to <12>.

<14> A near-infrared cut filter comprising: the cured film according to <13>.

<15> A solid-state imaging device comprising: the cured film according to <13>.

<16> An infrared sensor comprising: the cured film according to <13>.

<17> A compound which is represented by Formula (1):

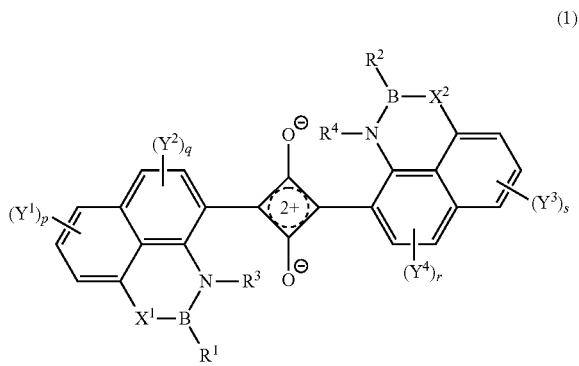

in the formula, R$^1$ and R$^2$ each independently represent an alkyl group, an alkenyl group, an aryl group, a heteroaryl group, or a group represented by Formula (W), at least one of R$^1$ or R$^2$ represents a group represented by Formula (W), R$^3$ and R$^4$ each independently represent a hydrogen atom or an alkyl group, X$^1$ and X$^2$ each independently represent an oxygen atom or —N(R$^5$)—, R$^5$ represents a hydrogen atom, an alkyl group, an aryl group, or a heteroaryl group, Y$^1$ to Y$^4$ each independently represent a substituent, each of Y$^1$ and Y$^2$, and Y$^3$ and Y$^4$ may be bonded to form a ring structure, in a case where the compound represented by Formula (1) has more than one of each of Y$^1$ to Y$^4$, these may be bonded to each other to form a ring structure, respectively, p and s each independently represent an integer of 0 to 3, and q and r each independently represent an integer of 0 to 2, and $$—S^1-L^1-T^1 \qquad (W)$$

in Formula (W), S$^1$ represents a single bond, an arylene group, or a heteroarylene group, L$^1$ represents an alkylene group, an alkenylene group, an alkynylene group, —O—, —S—, —NR$^{L1}$—, —CO—, —COO—, —OCO—, —CONR$^{L1}$—, —NR$^{L1}$CO—, —SO$_2$—, —OR$^{L2}$—, or a group obtained by combining two or more thereof, R$^{L1}$ represents a hydrogen atom or an alkyl group, R$^{L2}$ represents an alkylene group, T$^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group, in a case where S$^1$ is a single bond, L$^1$ is an alkylene group, and T$^1$ is an alkyl group, the total number of carbon atoms included in L$^1$ and T$^1$ is not less than 13, and in a case where S$^1$ is an arylene group, the total number of carbon atoms included in L$^1$ and T$^1$ is not less than 5.

According to the invention, it is possible to provide a near-infrared absorption composition which contains a squarylium compound having excellent solvent solubility, a cured film which uses the near-infrared absorption composition, a near-infrared cut filter, a solid-state imaging device, an infrared sensor, and a compound.

DESCRIPTION OF THE PREFERRED EMBODIMENTS

Figure 1:
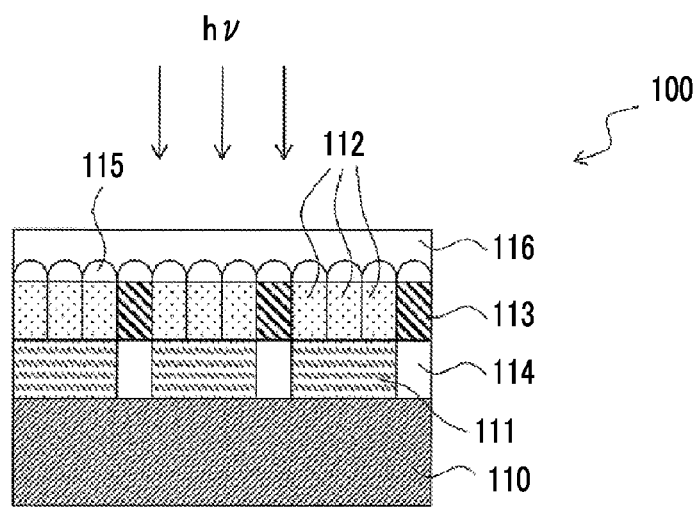
FIG. 1 is a cross-sectional view schematically illustrating a configuration of an infrared sensor according to an embodiment of the invention.

Hereinafter, the contents of the invention will be described in detail.

In this specification, the expression "to" is used to mean that numerical values before and after the expression are included as a lower limit value and an upper limit value.

In the description of a group (atomic group) in this specification, a denotation without substitution and unsubstitution includes a group (atomic group) with a substituent, together with a group (atomic group) without a substituent. For example, an "alkyl group" includes not only an alkyl group (unsubstituted alkyl group) without a substituent but also an alkyl group (substituted alkyl group) with a substituent.

In this specification, "(meth)acrylate" represents acrylate and methacrylate, "(meth)acryl" represents acryl and methacryl, and "(meth)acryloyl" represents acryloyl and methacryloyl.

In this specification, a polymerizable compound refers to a compound having a polymerizable functional group, and may be a monomer or a polymer. A polymerizable functional group refers to a group involved in a polymerization reaction.

A weight average molecular weight and a number average molecular weight of a compound used in the invention can be measured by gel permeation chromatography (GPC), and are defined as values in terms of polystyrene measured by GPC.

In this specification, a near-infrared ray refers to light with a maximum absorption wavelength region of 700 to 2,500 nm (electromagnetic wave).

In this specification, a total solid content refers to a total mass of components except for a solvent from the entire content of a composition. In the invention, a solid content is a solid content at 25° C.

<Near-Infrared Absorption Composition>

A near-infrared absorption composition according to the invention contains: a compound (hereinafter, also referred to as Compound (1)) represented by Formula (1) to be described later; and a resin.

By allowing Compound (1) to have a group represented by Formula (W), Compound (1) may be a compound having excellent solvent solubility. In addition, by allowing Compound (1) to have a group represented by Formula (W), film flexibility can be improved in the formation of a film.

The high heat resistance and the high light resistance of Compound (1) are derived from a boron atom of Compound (1). The reasons for the improvement in heat resistance and light resistance are presumed to be that since a boron complex is formed, planarity of molecules is improved, and aggregates in a coating film are stabilized. Furthermore, in a case where Formula (W) includes a long-chain alkyl structure, a compound having excellent solvent solubility and excellent moisture resistance can be made. The detailed mechanism thereof is not clear. However, the reasons for this are presumed to be that due to the interaction between long-chain alkyl structures, aggregates are stabilized and hydrophobicity is improved, whereby the moisture has little influence.

According to the invention, in the group represented by Formula (W), a -$L^1$-$T^1$ portion preferably includes a branched alkyl structure. According to this aspect, the solvent solubility of Compound (1) can be further improved.

According to the invention, in the group represented by Formula (W), the -$L^1$-$T^1$ portion preferably includes asymmetric carbon. According to this aspect, Compound (1) may include a plurality of optical isomers, and as a result, the solvent solubility of Compound (1) can be further improved.

According to the invention, the compound represented by Formula (1) preferably includes two or more types of optical isomers. That is, in a case where the compound represented by Formula (1) is a racemic mixture, the solvent solubility can be further improved.

Hereinafter, the invention will be described in detail.

<<<Compound Represented by Formula (1)>>>

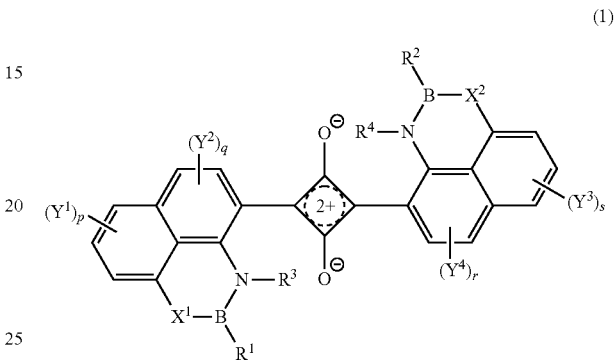

(1)

In the formula, $R^1$ and $R^2$ each independently represent an alkyl group, an alkenyl group, an aryl group, a heteroaryl group, or a group represented by the following Formula (W), and at least one of $R^1$ or $R^2$ represents a group represented by the following Formula (W).

$R^3$ and $R^4$ each independently represent a hydrogen atom or an alkyl group.

$X^1$ and $X^2$ each independently represent an oxygen atom or —N($R^5$)—.

$R^5$ represents a hydrogen atom, an alkyl group, an aryl group, or a heteroaryl group.

$Y^1$ to $Y^4$ each independently represent a substituent. Each of $Y^1$ and $Y^2$, and $Y^3$ and $Y^4$ may be bonded to form a ring structure.

In a case where the number of each of $Y^1$ to $Y^4$ is more than one, these may be bonded to each other to form a ring structure, respectively.

p and s each independently represent an integer of 0 to 3.
q and r each independently represent an integer of 0 to 2.

$$—S^1-L^1-T^1 \tag{W}$$

In Formula (W), $S^1$ represents a single bond, an arylene group, or a heteroarylene group.

$L^1$ represents an alkylene group, an alkenylene group, an alkynylene group, —O—, —S—, —$NR^{L1}$—, —CO—, —COO—, —OCO—, —$CONR^{L1}$—, —$NR^{L1}$ CO—, —$SO_2$—, —$OR^{L2}$—, or a group obtained by combining two or more thereof. $R^{L1}$ represents a hydrogen atom or an alkyl group, and $R^{L2}$ represents an alkylene group.

$T^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group.

In a case where $S^1$ is a single bond, $L^1$ is an alkylene group, and $T^1$ is an alkyl group, the total number of carbon atoms included in $L^1$ and $T^1$ is not less than 13.

In a case where $S^1$ is an arylene group, the total number of carbon atoms included in $L^1$ and $T^1$ is not less than 5.

In Formula (1), $R^1$ and $R^2$ each independently represent an alkyl group, an alkenyl group, an aryl group, a heteroaryl group, or a group represented by Formula (W) to be described later, and at least one of $R^1$ or $R^2$ represents a group represented by Formula (W). According to the invention, both of $R^1$ and $R^2$ are preferably groups represented by Formula (W).

$R^1$ and $R^2$ may be the same or different groups. According to the invention, $R^1$ and $R^2$ are preferably the same groups.

In this specification, an aryl group means an aromatic hydrocarbon group, and a heteroaryl group means an aromatic heterocyclic group.

The number of carbon atoms of the alkyl group represented by $R^1$ and $R^2$ is preferably 1 to 40. The lower limit thereof is more preferably not less than 3, even more preferably not less than 5, still more preferably not less than 10, and particularly preferably not less than 13. The upper limit thereof is more preferably not greater than 35, and even more preferably not greater than 30. The alkyl group may be linear, branched, or cyclic. The alkyl group is preferably linear or branched, and more preferably branched. The number of branches of a branched alkyl group is, for example, preferably 2 to 10, and more preferably 2 to 8. Satisfactory solvent solubility is obtained in a case where the number of branches is within the above-described range.

The number of carbon atoms of the alkenyl group represented by $R^1$ and $R^2$ is preferably 2 to 40. The lower limit thereof is, for example, more preferably not less than 3, even more preferably not less than 5, still more preferably not less than 8, and particularly preferably not less than 10. The upper limit thereof is more preferably not greater than 35, and even more preferably not greater than 30. The alkenyl group is preferably linear or branched, and more preferably branched. The number of branches of a branched alkenyl group is preferably 2 to 10, and more preferably 2 to 8. Satisfactory solvent solubility is obtained in a case where the number of branches is within the above-described range.

The number of carbon atoms of the aryl group represented by $R^1$ and $R^2$ is preferably 6 to 30, more preferably 6 to 20, and even more preferably 6 to 12.

The heteroaryl group represented by $R^1$ and $R^2$ may be monocyclic or polycyclic. The number of hetero atoms constituting the ring of the heteroaryl group is preferably 1 to 3. As the hetero atom constituting the ring of the heteroaryl group, a nitrogen atom, an oxygen atom, or a sulfur atom is preferable. The number of carbon atoms constituting the ring of the heteroaryl group is preferably 3 to 30, more preferably 3 to 18, and even more preferably 3 to 12.

(Group Represented by Formula (W))

Next, the group represented by Formula (W) will be described.

$$-S^1-L^1-T^1 \qquad (W)$$

In Formula (W), $S^1$ represents a single bond, an arylene group, or a heteroarylene group.

$L^1$ represents an alkylene group, an alkenylene group, an alkynylene group, —O—, —S—, —NR$^{L1}$—, —CO—, —COO—, —OCO—, —CONR$^{L1}$—, —NR$^{L1}$CO—, —SO$_2$—, —OR$^{L2}$—, or a group obtained by combining two or more thereof. $R^{L1}$ represents a hydrogen atom or an alkyl group, and $R^{L2}$ represents an alkylene group.

$T^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group.

In a case where $S^1$ is a single bond, $L^1$ is an alkylene group, and $T^1$ is an alkyl group, the total number of carbon atoms included in $L^1$ and $T^1$ is not less than 13.

In a case where $S^1$ is an arylene group, the total number of carbon atoms included in $L^1$ and $T^1$ is not less than 5.

In Formula (W), $S^1$ represents a single bond, an arylene group, or a heteroarylene group, and from the viewpoint of stability of bonding to a boron atom, an arylene group or a heteroarylene group is preferable, and an arylene group is more preferable.

The arylene group may be monocyclic or polycyclic, and is preferably monocyclic. The number of carbon atoms of the arylene group is preferably 6 to 20, and more preferably 6 to 12.

The heteroaryl group may be monocyclic or polycyclic, and is preferably monocyclic. The number of hetero atoms constituting the ring of the heteroaryl group is preferably 1 to 3. As the hetero atom constituting the ring of the heteroaryl group, a nitrogen atom, an oxygen atom, a sulfur atom, or a selenium atom is preferable. The number of carbon atoms constituting the ring of the heteroaryl group is preferably 3 to 30, more preferably 3 to 18, and even more preferably 3 to 12.

Specific examples of the arylene group and the heteroarylene group represented by $S^1$ include the following structures.

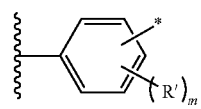

(S-1)

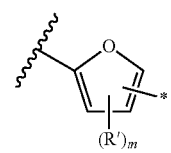

(S-2)

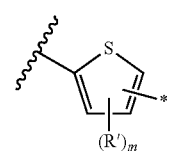

(S-3)

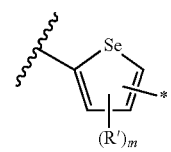

(S-4)

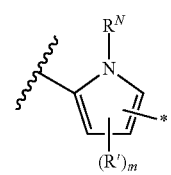

(S-5)

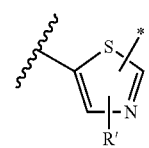

(S-6)

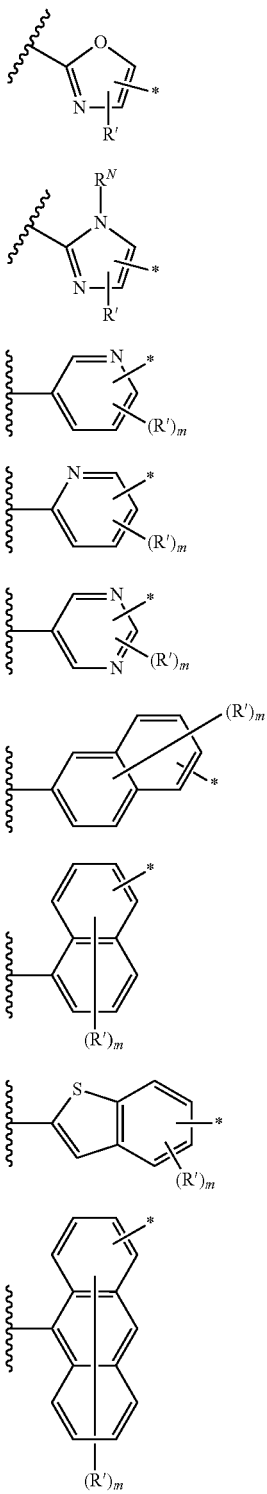

In the formulae, a wavy line portion represents a bonding position to a boron atom of Formula (1). * represents a bonding position to $L^1$. $R'$ represents a substituent. $R^N$ represents a hydrogen atom or an alkyl group. m represents an integer of 0 or more.

Examples of the substituent represented by $R'$ include substituents to be described in the following description of $R^6$ to $R^8$.

The number of carbon atoms of the alkyl group represented by $R^N$ is preferably 1 to 20, more preferably 1 to 10, even more preferably 1 to 4, and particularly preferably 1 or 2. The alkyl group may be linear or branched.

m represents an integer of 0 or more. The upper limit of m is the maximum number of substitutions of each group. m is preferably 0.

In Formula (W), $L^1$ represents an alkylene group, an alkenylene group, an alkynylene group, —O—, —S—, —$NR^{L1}$—, —CO—, —COO—, —OCO—, —$CONR^{L1}$—, —$NR^{L1}CO$—, —$SO_2$—, —$OR^{L2}$—, or a group obtained by combining two or more thereof. $R^{L1}$ represents a hydrogen atom or an alkyl group, and $R^{L2}$ represents an alkylene group.

In Formula (W), $L^1$ is preferably an alkylene group, an alkenylene group, an alkynylene group, —O—, —S—, —$NR^{L1}$—, —COO—, —OCO—, —$CONR^{L1}$—, —$SO_2$—, —$OR^{L2}$—, or a group obtained by combining two or more thereof. From the viewpoint of flexibility and solvent solubility, $L^1$ is more preferably an alkylene group, an alkenylene group, —O—, —$OR^{L2}$—, or a group obtained by combining two or more thereof, even more preferably an alkylene group, an alkenylene group, —O—, or —$OR^{L2}$—, and still more preferably an alkylene group, —O—, or —$OR^{L2}$—.

The number of carbon atoms of the alkylene group represented by $L^1$ is preferably 1 to 40. The lower limit thereof is more preferably not less than 3, even more preferably not less than 5, still more preferably not less than 10, and particularly preferably not less than 13. The upper limit thereof is more preferably not greater than 35, and even more preferably not greater than 30. The alkylene group may be linear, branched, or cyclic. The alkylene group is preferably linear or branched, and particularly preferably branched. The number of branches of a branched alkylene group is, for example, preferably 2 to 10, and more preferably 2 to 8. Satisfactory solvent solubility is obtained in a case where the number of branches is within the above-described range.

The number of carbon atoms of the alkenylene group and the alkynylene group represented by $L^1$ is preferably 2 to 40. The lower limit thereof is, for example, more preferably not less than 3, even more preferably not less than 5, still more preferably not less than 8, and particularly preferably not less than 10. The upper limit thereof is more preferably not greater than 35, and even more preferably not greater than 30. The alkenylene group and the alkynylene group may be linear or branched. The alkenylene group and the alkynylene group are preferably linear or branched, and particularly preferably branched. The number of branches of a branched alkenylene group or alkynylene group is preferably 2 to 10, and more preferably 2 to 8. Satisfactory solvent solubility is obtained in a case where the number of branches is within the above-described range.

$R^{L1}$ represents a hydrogen atom or an alkyl group, and is preferably a hydrogen atom. The number of carbon atoms of the alkyl group is preferably 1 to 20, more preferably 1 to 10, even more preferably 1 to 4, and particularly preferably 1 or 2. The alkyl group may be linear or branched.

$R^{L2}$ represents an alkylene group. The alkylene group represented by $R^{L2}$ is synonymous with the alkylene group described in the description of $L^1$, and its preferable ranges are also similar to those in the description of $L^1$.

In Formula (W), $T^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group.

The number of carbon atoms of the alkyl group or the alkyl group of the trialkylsilyl group and the trialkoxysilyl group is preferably 1 to 40. The lower limit thereof is more preferably not less than 3, even more preferably not less than 5, still more preferably not less than 10, and particularly preferably not less than 13. The upper limit thereof is more preferably not greater than 35, and even more preferably not greater than 30. The alkyl group may be linear, branched, or cyclic, and is preferably linear or branched.

The aryl group and the heteroaryl group are synonymous with the aryl group and the heteroaryl group described in the description of $R^1$ and $R^2$, and their preferable ranges are also similar to those in the description of $R^1$ and $R^2$.

In Formula (W), in a case where $S^1$ is a single bond, $L^1$ is an alkylene group, and $T^1$ is an alkyl group, the total number of carbon atoms included in $L^1$ and $T^1$ is not less than 13. The total number of carbon atoms included in $L^1$ and $T^1$ is preferably not less than 21 from the viewpoint of solvent solubility. The upper limit is, for example, preferably not greater than 40, and more preferably not greater than 35.

In a case where $S^1$ is an arylene group, the total number of carbon atoms included in $L^1$ and $T^1$ is not less than 5. From the viewpoint of solvent solubility, the total number of carbon atoms included in $L^1$ and $T^1$ is preferably not less than 9, and more preferably not less than 10. The upper limit is, for example, preferably not greater than 40, and more preferably not greater than 35.

According to the invention, a preferable aspect of Formula (W) is a combination in which $S^1$ is an arylene group or a heteroarylene group, $L^1$ is an alkylene group, an alkenylene group, an alkynylene group, —O—, —S—, —NR$^{L1}$—, —COO—, —OCO—, —CONR$^{L1}$—, —SO$_2$—, —OR$^{L2}$—, or a group obtained by combining two or more thereof, and $T^1$ is an alkyl group or a trialkylsilyl group. $S^1$ is more preferably an arylene group. $L^1$ is more preferably an alkylene group, an alkenylene group, —O—, —OR$^{L2}$—, or a group obtained by combining two or more thereof, even more preferably an alkylene group, an alkenylene group, —O—, or —OR$^{L2}$—, and particularly preferably an alkylene group, —O— or —OR$^{L2}$—. $T^1$ is more preferably an alkyl group.

In Formula (W), the -$L^1$-$T^1$ portion preferably includes a branched alkyl structure. Specifically, the -$L^1$-$T^1$ portion is particularly preferably a branched alkyl group or a branched alkoxy group. The number of branches of the -$L^1$-$T^1$ portion is preferably 2 to 10, and more preferably 2 to 8. The number of carbon atoms of the -$L^1$-$T^1$ portion is preferably not less than 5, more preferably not less than 9, and even more preferably not less than 10. The upper limit is, for example, preferably not greater than 40, and more preferably not greater than 35.

In Formula (W), the -$L^1$-$T^1$ portion preferably includes asymmetric carbon. According to this aspect, Compound (1) may include a plurality of optical isomers, and as a result, the solvent solubility of Compound (1) can be further improved. The number of asymmetric carbon atoms is preferably not less than 1. The upper limit of the number of asymmetric carbon atoms is not particularly limited, but preferably not greater than 4.

Specific examples of the group represented by Formula (W) are as follows. In the following structural formulae, A is a portion for connecting to a boron atom of Formula (1). In the following structural formulae, * represents asymmetric carbon, a wavy line represents two types of configurations of methyl groups, and a structural formula has a racemic body.

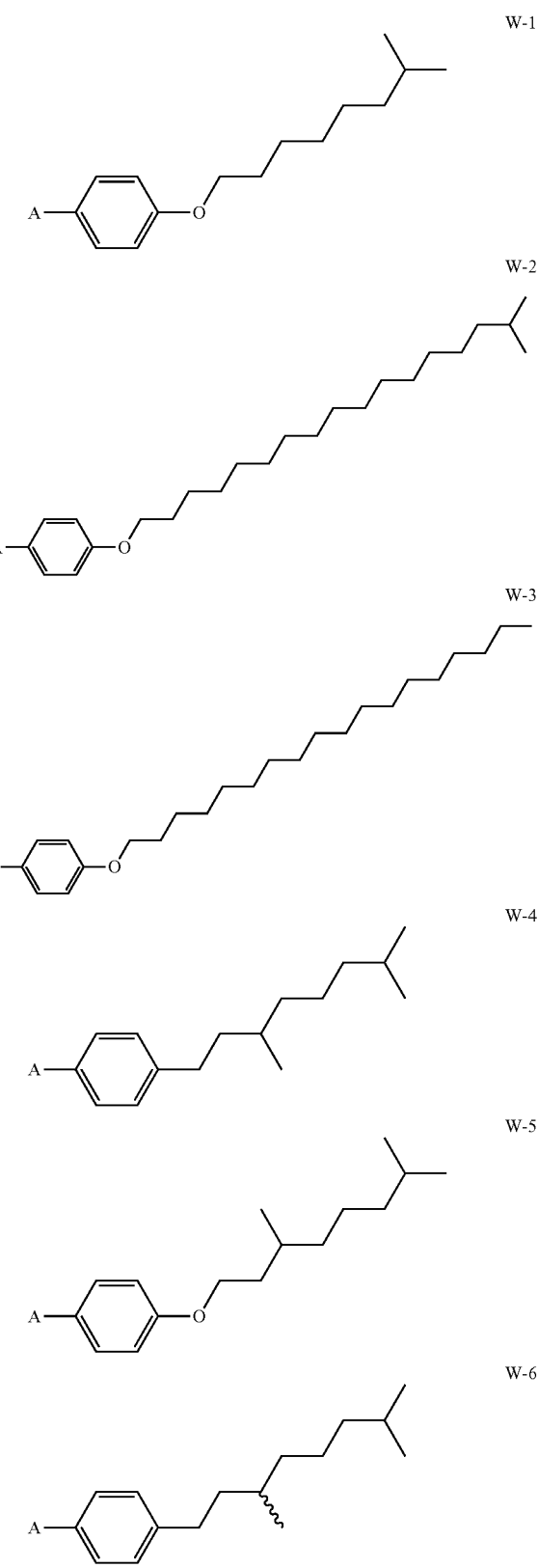

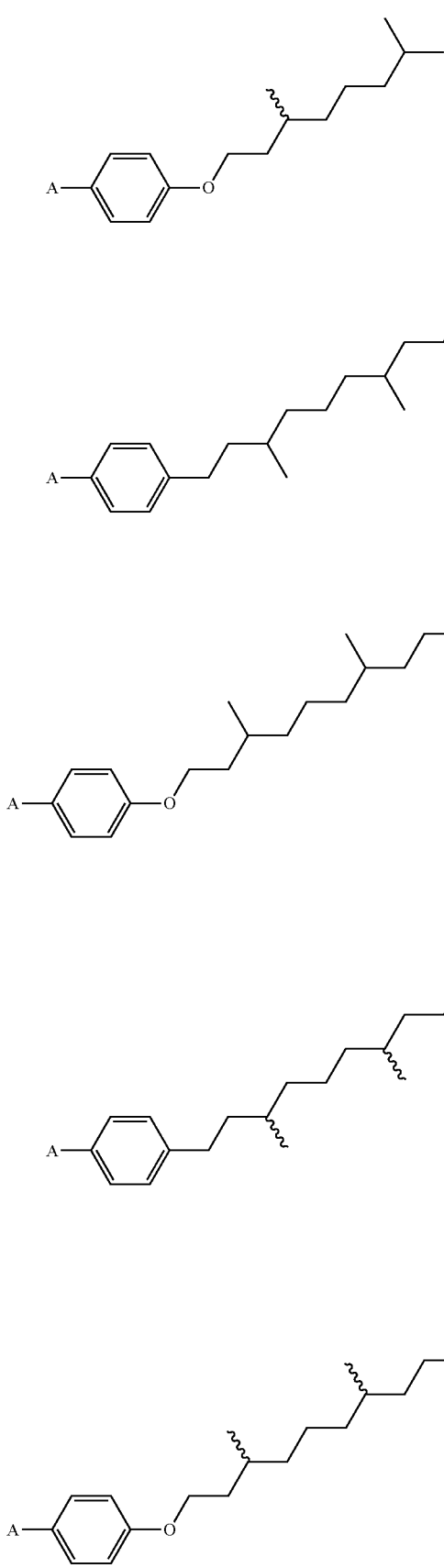
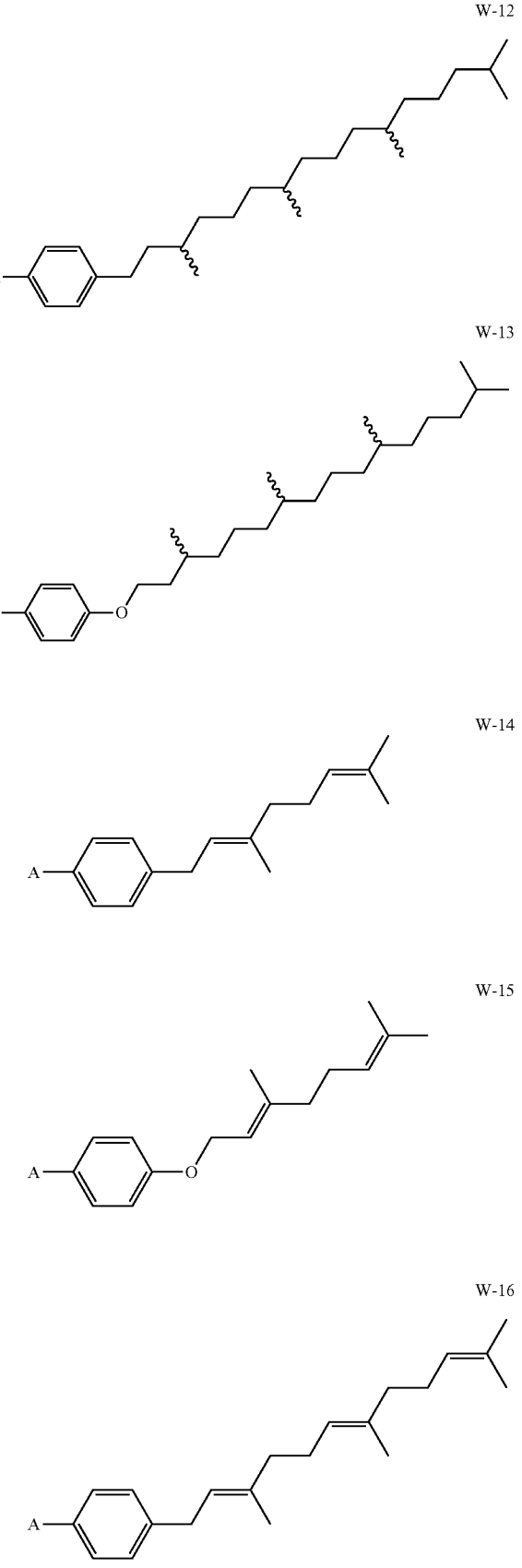

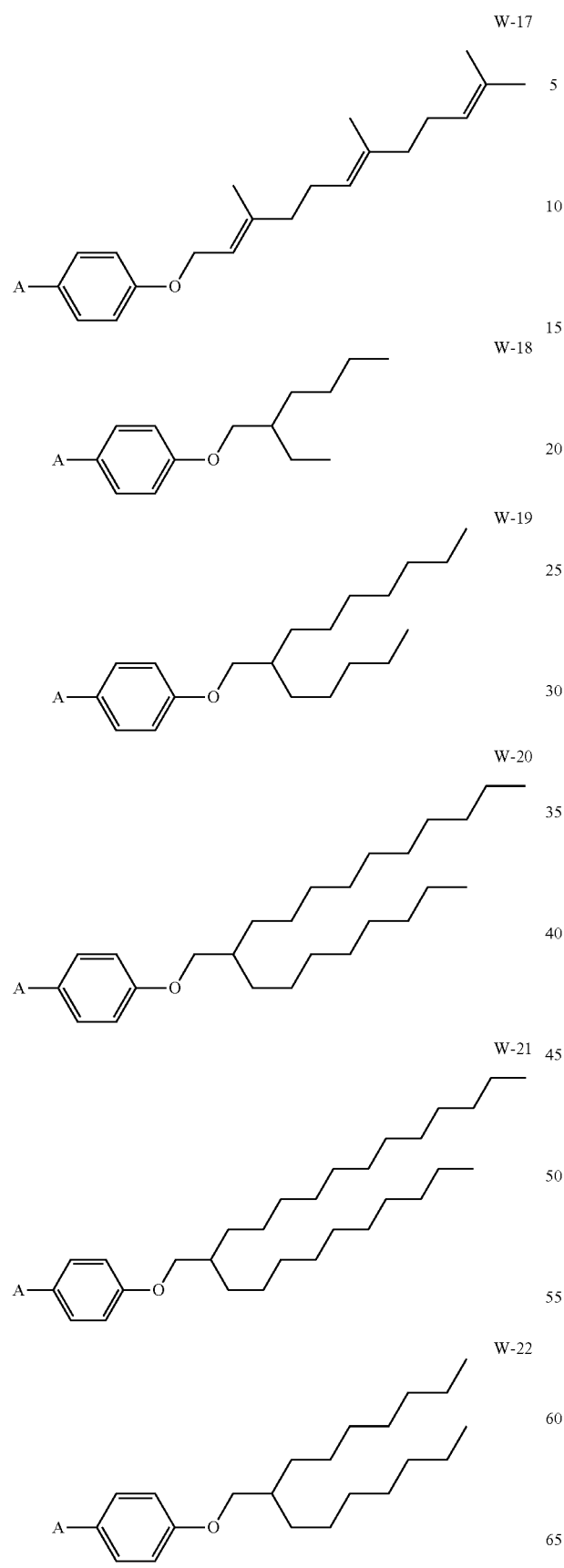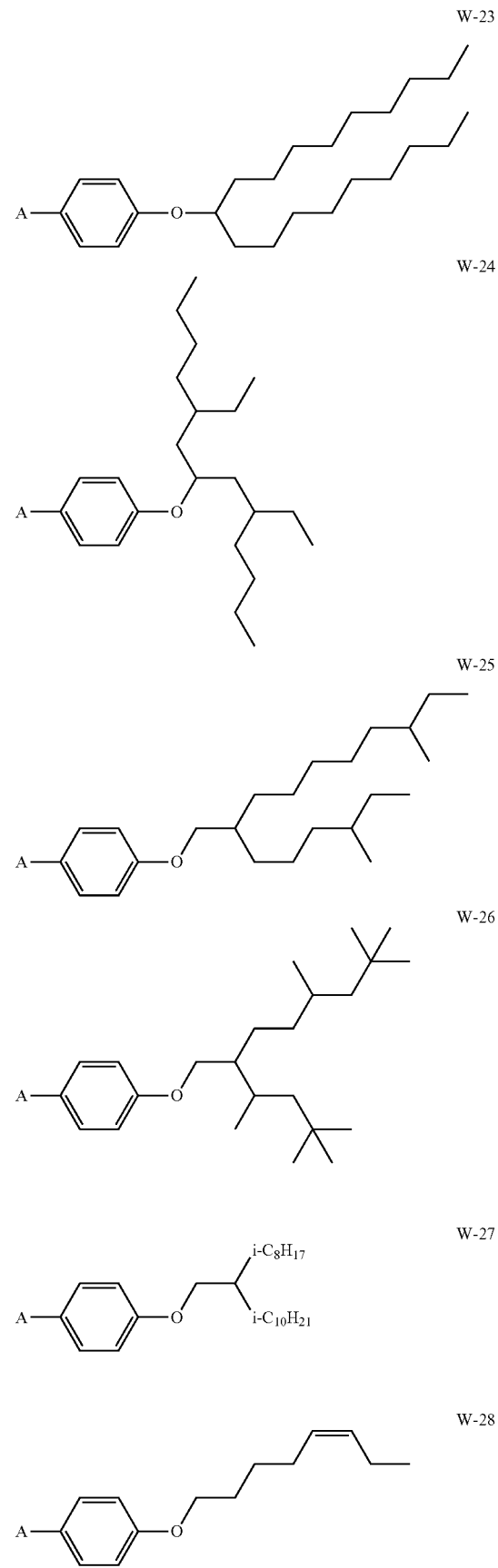

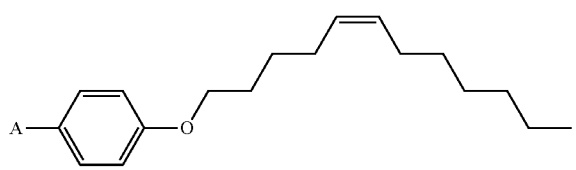
W-29

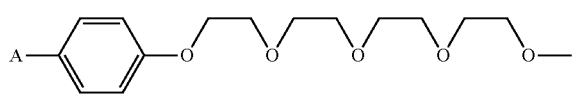
W-30

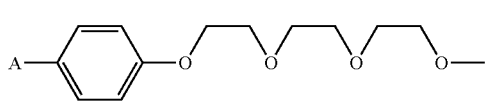
W-31

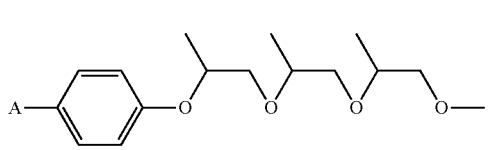
W-32

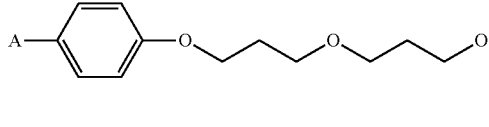
W-33

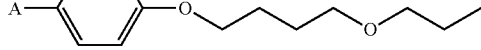
W-34

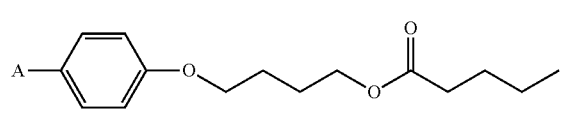
W-35

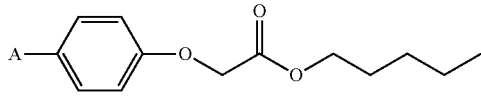
W-36

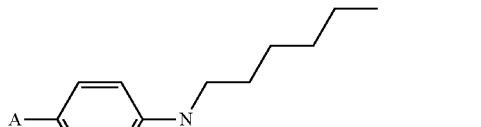
W-37

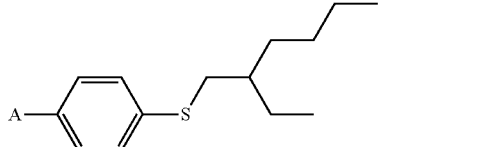
W-38

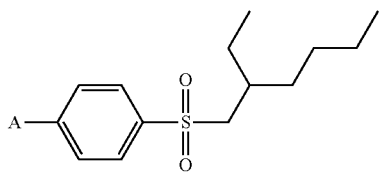
W-39

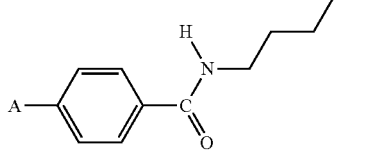
W-40

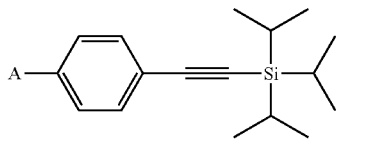
W-41

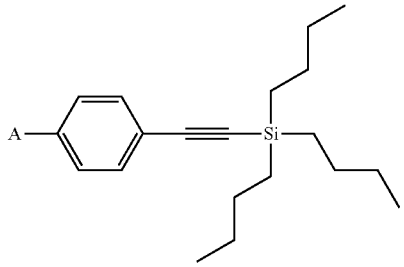
W-42

In Formula (1), $R^3$ and $R^4$ each independently represent a hydrogen atom or an alkyl group. $R^3$ and $R^4$ may be the same as or different from each other. According to the invention, $R^3$ and $R^4$ are preferably the same as each other.

The number of carbon atoms of the alkyl group represented by $R^3$ and $R^4$ is preferably 1 to 20, more preferably 1 to 10, even more preferably 1 to 4, and particularly preferably 1 or 2. The alkyl group may be linear or branched. Specific examples thereof include a methyl group, an ethyl group, a propyl group, an isopropyl group, a butyl group, and an isobutyl group.

$R^3$ and $R^4$ each are independently preferably a hydrogen atom, a methyl group, or an ethyl group, more preferably a hydrogen atom or a methyl group, and particularly preferably a hydrogen atom.

In Formula (1), $X^1$ and $X^2$ each independently represent an oxygen atom (—O—) or —N($R^5$)—. $X^1$ and $X^2$ may be the same as or different from each other, and are preferably the same as each other.

$R^5$ represents a hydrogen atom, an alkyl group, an aryl group, or a heteroaryl group. $R^5$ is preferably a hydrogen atom, an alkyl group, or an aryl group. The alkyl group, the aryl group, and the heteroaryl group represented by $R^5$ may be unsubstituted or may have a substituent. Examples of the substituent include substituents to be described in the following description of $R^6$ to $R^8$.

The number of carbon atoms of the alkyl group is preferably 1 to 20, more preferably 1 to 10, even more preferably 1 to 4, and particularly preferably 1 or 2. The alkyl group may be linear or branched.

The number of carbon atoms of the aryl group is preferably 6 to 20, and more preferably 6 to 12.

The heteroaryl group may be monocyclic or polycyclic. The number of hetero atoms constituting the ring of the heteroaryl group is preferably 1 to 3. As the hetero atom constituting the ring of the heteroaryl group, a nitrogen atom, an oxygen atom, or a sulfur atom is preferable. The number of carbon atoms constituting the ring of the heteroaryl group is preferably 3 to 30, more preferably 3 to 18, and even more preferably 3 to 12.

$X^1$ and $X^2$ each are independently preferably an oxygen atom, or represented by any one of the following structural formulae.

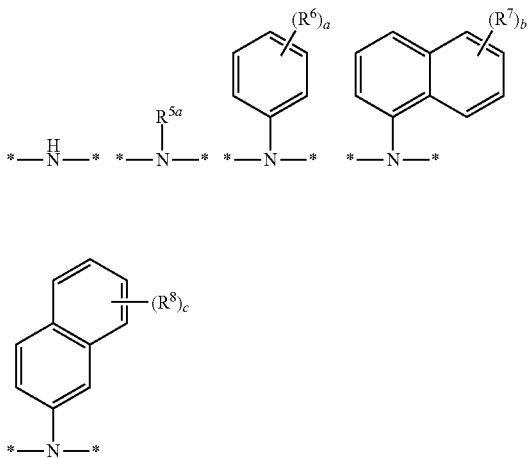

In the formulae, $R^{5a}$ represents an alkyl group. $R^6$ to $R^8$ each independently represent a substituent. a represents an integer of 0 to 5. b and c each represent an integer of 0 to 7. * represents a bond.

Examples of the substituent represented by $R^6$ to $R^8$ include a halogen atom, a cyano group, a nitro group, an alkyl group, an alkenyl group, an alkynyl group, an aryl group, a heteroaryl group, an aralkyl group, an alkoxy group, an aryloxy group, a heteroaryloxy group, an alkylthio group, an arylthio group, a heteroarylthio group, $-NR^{a1}R^{a2}$, $-COR^{a3}$, $-COOR^{a4}$, $-OCOR^{a5}$, $-NHCOR^{a6}$, $-CONR^{a7}R^{a8}$, $-NHCONR^{a9}R^{a10}$, $-NHCOOR^{a11}$, $-SO_2R^{a12}$, $-SO_2OR^{a13}$, $-NHSO_2R^{a14}$, and $-SO_2NR^{a15}R^{a16}$. $R^{a1}$ to $R^{a16}$ each independently represent a hydrogen atom, an alkyl group, an alkenyl group, an alkynyl group, an aryl group, or a heteroaryl group.

Examples of the halogen atom include a fluorine atom, a chlorine atom, a bromine atom, and an iodine atom.

The number of carbon atoms of the alkyl group, the alkoxy group, and the alkylthio group is preferably 1 to 20, more preferably 1 to 15, and even more preferably 1 to 8. The alkyl group may be linear, branched, or cyclic, and is preferably linear or branched.

The number of carbon atoms of the alkenyl group is preferably 2 to 20, more preferably 2 to 12, and even more preferably 2 to 8. The alkenyl group may be linear, branched, or cyclic, and is preferably linear or branched.

The number of carbon atoms of the alkynyl group is preferably 2 to 40, more preferably 2 to 30, and even more preferably 2 to 25. The alkynyl group may be linear, branched, or cyclic, and is preferably linear or branched.

The number of carbon atoms of the aryl group is preferably 6 to 30, more preferably 6 to 20, and even more preferably 6 to 12.

Examples of the aryl group of the aryloxy group and the arylthio group are as described above, and its preferable ranges are also similar to those in the above description.

The number of carbon atoms of the aralkyl group is preferably 7 to 40, more preferably 7 to 30, and even more preferably 7 to 25.

The heteroaryl group is preferably monocyclic or fused, more preferably monocyclic or fused with a fused number of 2 to 8, and even more preferably monocyclic or fused with a fused number of 2 to 4. The number of hetero atoms constituting the ring of the heteroaryl group is preferably 1 to 3. As the hetero atom constituting the ring of the heteroaryl group, a nitrogen atom, an oxygen atom, or a sulfur atom is preferable. The heteroaryl group is preferably a 5-membered ring or a 6-membered ring.

Examples of the heteroaryl group of the heteroaryloxy group and the heteroarylthio group are as described above, and its preferable ranges are also similar to those in the above description.

In Formula (1), $Y^1$ to $Y^4$ each independently represent a substituent.

Examples of the substituent include a halogen atom, a cyano group, a nitro group, an alkyl group, an alkenyl group, an alkynyl group, an aryl group, a heteroaryl group, an aralkyl group, an alkoxy group, an aryloxy group, a heteroaryloxy group, an alkylthio group, an arylthio group, a heteroarylthio group, $-NR^{a1}R^{a2}$, $-COR^{a3}$, $-COOR^{a4}$, $-OCOR^{a5}$, $-NHCOR^{a6}$, $-CONR^{a7}R^{a8}$, $-NHCONR^{a9}R^{a10}$, $-NHCOOR^{a11}$, $-SO_2R^{a12}$, $-SO_2OR^{a13}$, $-NHSO_2R^{a14}$, and $-SO_2NR^{a15}R^{a16}$. $R^{a1}$ to $R^{a16}$ each independently represent a hydrogen atom, an alkyl group, an alkenyl group, an alkynyl group, an aryl group, or a heteroaryl group.

Details of the substituent are as described above in the description of $R^6$ to $R^8$.

Each of $Y^1$ and $Y^2$, and $Y^3$ and $Y^4$ may be bonded to form a ring structure. For example, $Y^1$ and $Y^2$ may be bonded to each other to form a tricyclic ring such as an acenaphthene ring or an acenaphthylene ring together with a naphthalene ring directly bonded to $Y^1$ and $Y^2$.

In a case where there are plural $Y^1$'s, $Y^2$'s, $Y^3$'s, and $Y^4$'s, $Y^1$'s, $Y^2$'s, $Y^3$'s, and $Y^4$'s may be bonded to each other to form a ring structure, respectively. For example, in a case where there are plural $Y^1$'s, the plural $Y^1$'s may be bonded to each other to form a tricyclic ring such as an anthracene ring or a phenanthrene ring together with a naphthalene ring directly bonded to $Y^1$ and $Y^2$. In a case where plural $Y^1$'s are bonded to each other to form a ring structure, plural $Y^2$'s, $Y^3$'s, and $Y^4$'s as substituents other than $Y^1$ may not necessarily exist. In addition, $Y^2$ to $Y^4$ may not exist. These are also the same as in a case where plural $Y^2$'s, plural $Y^3$'s, or plural $Y^4$'s are bonded to each other to form a ring structure, respectively.

p and s each independently represent an integer of 0 to 3, preferably 0 to 1, and particularly preferably 0.

q and r each independently represent an integer of 0 to 2, preferably 0 to 1, and particularly preferably 0.

In Formula (1), a cation is delocalized as follows.
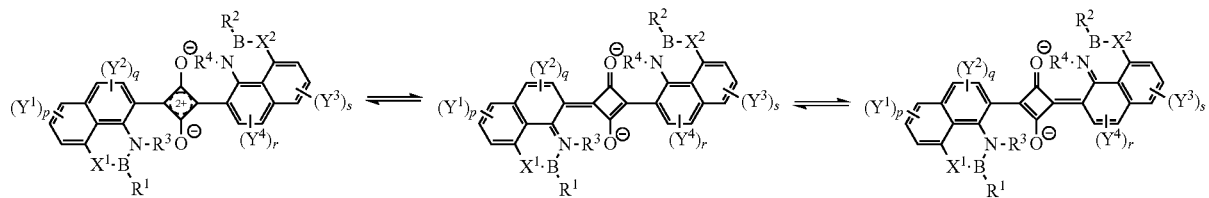
Specific examples of the compound represented by Formula (1) include the following compounds. In the following formulae, a wavy line represents two types of configurations of methyl groups, and a structural formula has a racemic body. * represents asymmetric carbon.
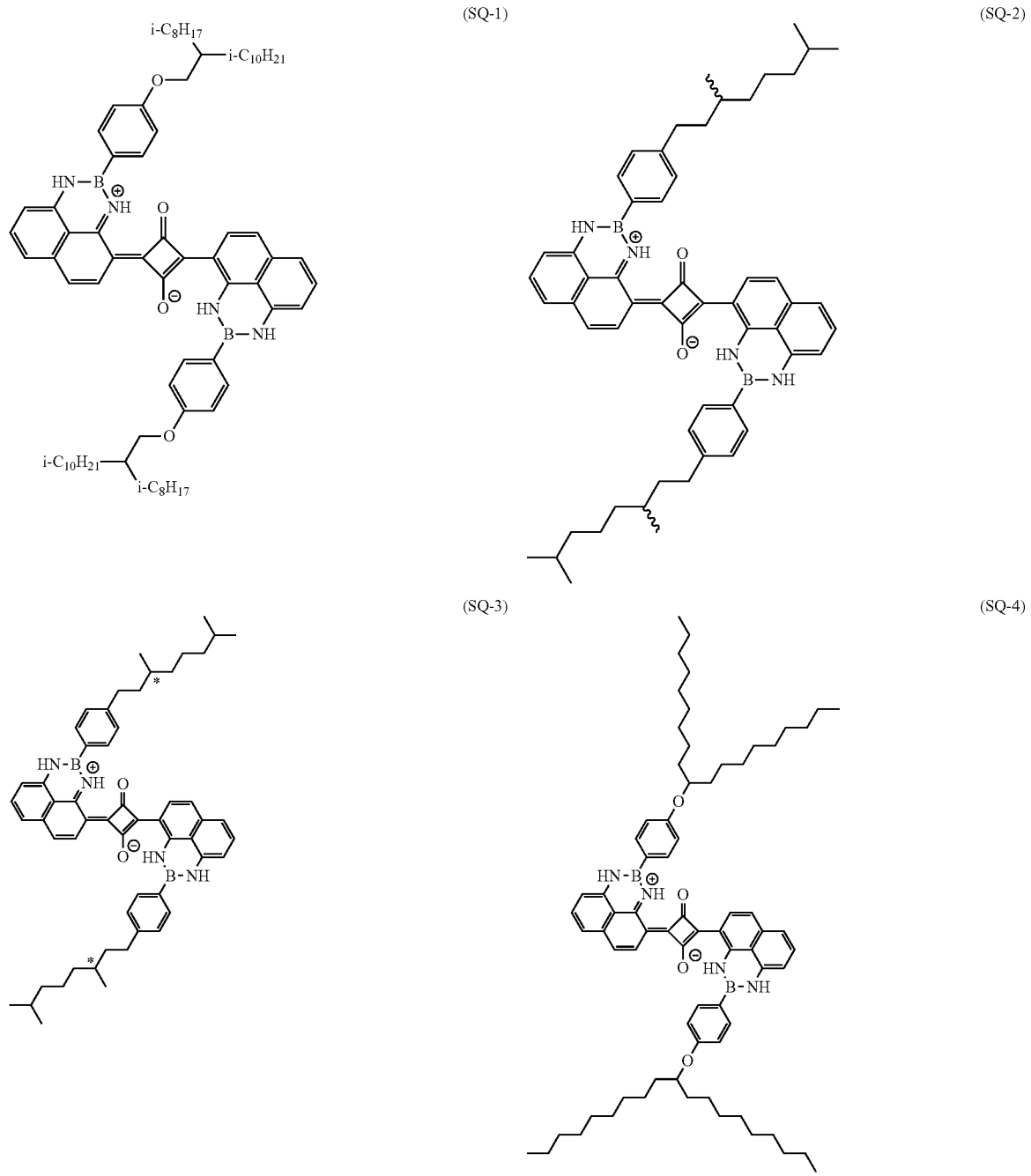

(SQ-5)
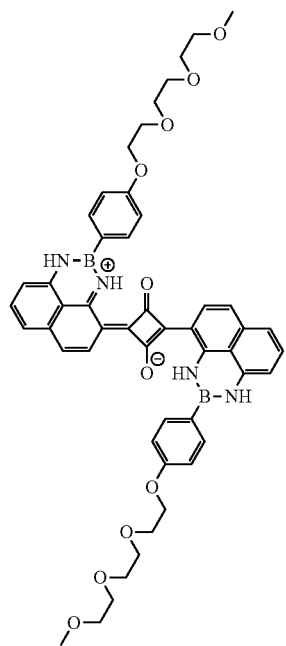
(SQ-6)

-continued
(SQ-7)
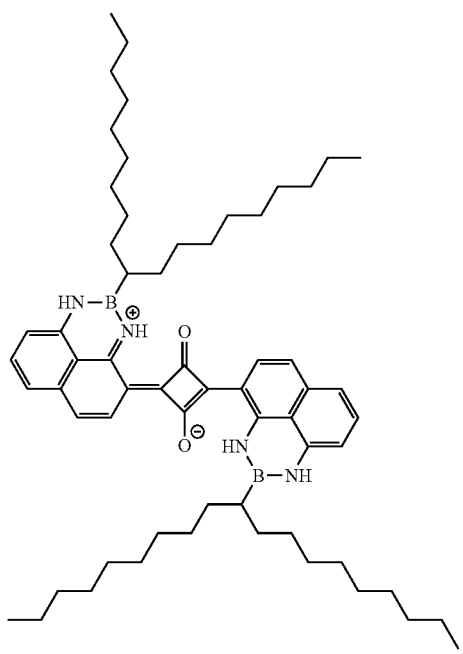
(SQ-8)
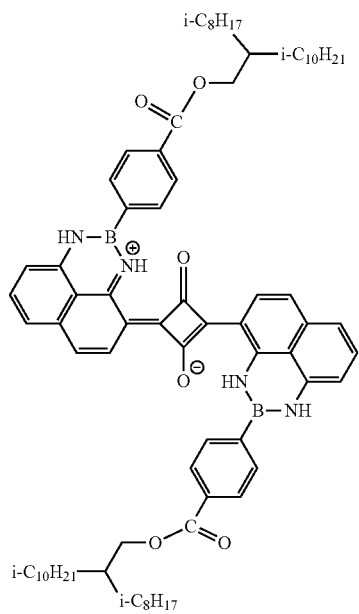
(SQ-9)
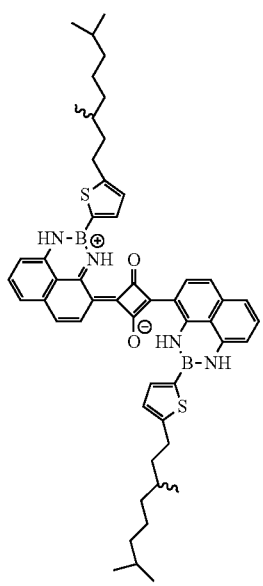
(SQ-10)
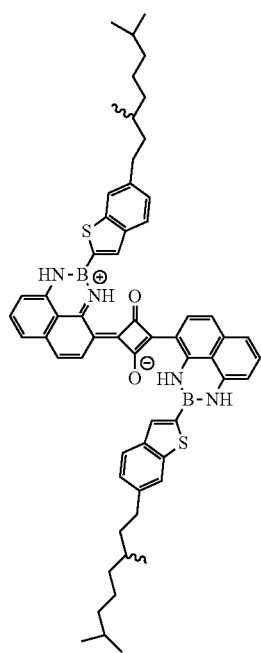

(SQ-11)

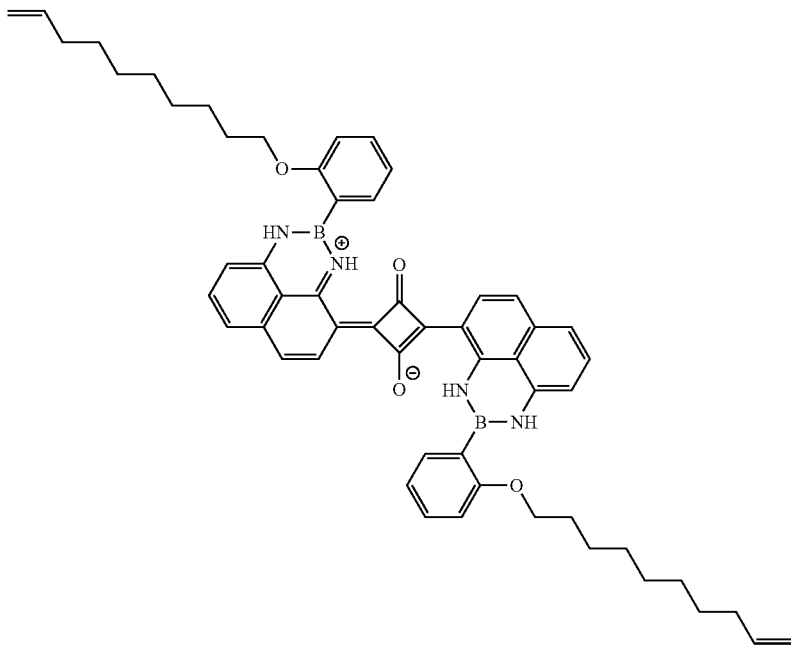

The molecular weight of the compound represented by Formula (1) is preferably 500 to 3,000, and more preferably 700 to 2,000.

The compound represented by Formula (1) preferably has a maximum absorption wavelength at a wavelength of 700 to 1,200 nm, and more preferably has a maximum absorption wavelength at a wavelength of 750 to 1,000 nm.

According to the invention, the value of the maximum absorption wavelength is obtained as follows: a compound represented by Formula (1) is dissolved in tetrahydrofuran to prepare a solution with a concentration of 1 g/L, and an absorption spectrum of the solution obtained by dissolving the compound is measured in a wavelength range of 350 nm to 1,200 nm using UV-1800 manufactured by Shimadzu Corporation.

The molar light absorption coefficient of the compound represented by Formula (1) is not limited, but preferably 5,000 to 250,000, and more preferably 50,000 to 200,000.

Although the compound represented by Formula (1) is preferably transparent, it may be slightly colored in green, gray, brown, or the like.

The near-infrared absorption composition according to the invention preferably contains the compound represented by Formula (1) in an amount of 5 to 90 mass % with respect to the total solid content of the near-infrared absorption composition. The lower limit of the amount is preferably not less than 10 mass %, and more preferably not less than 20 mass %. The upper limit of the amount is preferably not greater than 85 mass %, and more preferably not greater than 80 mass %.

<Resin>

The near-infrared absorption composition according to the invention includes a resin. The weight average molecular weight (Mw) of the resin is preferably 2,000 to 2,000,000. The upper limit thereof is more preferably not greater than 1,000,000, and even more preferably not greater than 500,000. The lower limit thereof is more preferably not less than 3,000, and even more preferably not less than 5,000.

In a case of an epoxy resin, the weight average molecular weight (Mw) of the epoxy resin is preferably not less than 100, and more preferably 200 to 2,000,000. The upper limit thereof is even more preferably not greater than 1,000,000, and still more preferably not greater than 500,000. The lower limit thereof is even more preferably not less than 100, and still more preferably not less than 200.

Examples of the resin include a (meth)acrylic resin, an epoxy resin, an ene-thiol resin, a polycarbonate resin, a polyether resin, a polyarylate resin, a polysulfone resin, a polyethersulfone resin, a polyparaphenylene resin, a polyarylene ether phosphine oxide resin, a polyimide resin, a polyamide-imide resin, a polyolefin resin, a cyclic olefin resin, and a polyester resin. These resins may be used singly, or as a mixture of two or more types thereof.

Among these, an acrylic resin, a polyester resin, and an epoxy resin are preferable, and an acrylic resin is more preferable from the viewpoint of solubility to the resin of Compound (1) and visible transparency.

Examples of the (meth)acrylic resin include a polymer including a constituent unit derived from at least one of a (meth)acrylic acid and its esters. Specifically, a polymer obtained by polymerizing at least one selected from a (meth)acrylic acid, (meth)acrylic acid esters, (meth)acrylamide, and (meth)acrylonitrile is exemplified.

Examples of the polyester resin include polymers obtained by the reaction between polyols (for example, ethylene glycol, propylene glycol, glycerin, and trimethylolpropane) and polybasic acids (for example, aromatic dicarboxylic acids such as a terephthalic acid, an isophthalic acid, and a naphthalene dicarboxylic acid, aromatic dicarboxylic acids in which a hydrogen atom of an aromatic nucleus of the above aromatic dicarboxylic acids is substituted with a methyl group, an ethyl group, a phenyl group, or the like, aliphatic dicarboxylic acids having 2 to 20 carbon atoms such as an adipic acid, a sebacic acid, and a dodecanedicarboxylic acid, and alicyclic dicarboxylic acids such as a cyclohexane dicarboxylic acid), and polymers (for example, polycaprolactone) obtained by ring-opening polymerization of circular ester compounds such as a caprolactone monomer.

Examples of the epoxy resin include bisphenol A epoxy resins, bisphenol F epoxy resins, phenol novolac epoxy resins, cresol novolac epoxy resins, and aliphatic epoxy resins. Commercially available products thereof are as follows.

Examples of the bisphenol A epoxy resins include JER 827, JER 828, JER 834, JER 1001, JER 1002, JER 1003, JER 1055, JER 1007, JER 1009, JER 1010 (all manufactured by Mitsubishi Chemical Corporation), EPICLON 860, EPICLON 1050, EPICLON 1051, and EPICLON 1055 (all manufactured by DIC Corporation).

Examples of the bisphenol F epoxy resins include JER 806, JER 807, JER 4004, JER 4005, JER 4007, JER 4010 (all manufactured by Mitsubishi Chemical Corporation), EPICLON 830, EPICLON 835 (all manufactured by DIC Corporation), LCE-21, and RE-602S (all manufactured by Nippon Kayaku Co., Ltd.).

Examples of the phenol novolac epoxy resins include JER 152, JER 154, JER 157S70, JER 157S65 (all manufactured by Mitsubishi Chemical Corporation), EPICLON N-740, EPICLON N-770, and EPICLON N-775 (all manufactured by DIC Corporation).

Examples of the cresol novolac epoxy resins include EPICLON N-660, EPICLON N-665, EPICLON N-670, EPICLON N-673, EPICLON N-680, EPICLON N-690, EPICLON N-695 (all manufactured by DIC Corporation), and EOCN-1020 (all manufactured by Nippon Kayaku Co., Ltd.).

Examples of the aliphatic epoxy resins include ADEKA RESIN EP-4080S, ADEKA RESIN EP-4085S, ADEKA RESIN EP-4088S (all manufactured by ADEKA Corporation), CELLOXIDE 2021P, CELLOXIDE 2081, CELLOXIDE 2083, CELLOXIDE 2085, EHPE3150, EPOLEAD PB 3600, EPOLEAD PB 4700 (all manufactured by DAICEL Corporation), DENACOL EX-212L, EX-214L, EX-216L, EX-321L, and EX-850L (all manufactured by Nagase ChemteX Corporation).

ADEKA RESIN EP-4000S, ADEKA RESIN EP-4003S, ADEKA RESIN EP-4010S, ADEKA RESIN EP-4011S (all manufactured by ADEKA Corporation), NC-2000, NC-3000, NC-7300, XD-1000, EPPN-501, EPPN-502 (all manufactured by ADEKA Corporation), and JER 1031S (manufactured by Mitsubishi Chemical Corporation) are also included.

The resin may have a group (hereinafter, also referred to as an acid group) promoting alkali solubility. Examples of the acid group include a carboxy group, a phosphate group, a sulfonate group, and a phenolic hydroxy group. These acid groups may be used singly, or two or more types thereof may be used. The resin having a group promoting alkali solubility is also referred to as an alkali-soluble resin.

As the alkali-soluble resin, a polymer having a carboxy group on a side chain is preferable, and examples thereof include alkali-soluble phenolic resins such as a methacrylic acid copolymer, an acrylic acid copolymer, an itaconic acid copolymer, a crotonic acid copolymer, a maleic acid copolymer, a partially esterified maleic acid copolymer, and a novolac resin, acid cellulose derivatives having a carboxy group on a side chain, and polymers having a hydroxy group with an acid anhydride added thereto. Particularly, copolymers of a (meth)acrylic acid with other monomers copolymerizable with the (meth)acrylic acid are preferable as the alkali-soluble resin. Examples of other monomers copolymerizable with a (meth)acrylic acid include alkyl (meth)acrylate, aryl (meth)acrylate, and a vinyl compound. Examples of the alkyl (meth)acrylate and the aryl (meth)acrylate include methyl (meth)acrylate, ethyl (meth)acrylate, propyl (meth)acrylate, butyl (meth)acrylate, isobutyl (meth)acrylate, pentyl (meth)acrylate, hexyl (meth)acrylate, octyl (meth)acrylate, phenyl (meth)acrylate, benzyl (meth)acrylate, tolyl (meth)acrylate, naphthyl (meth)acrylate, and cyclohexyl (meth)acrylate. Examples of the vinyl compound include styrene, α-methylstyrene, vinyl toluene, glycidyl methacrylate, acrylonitrile, vinyl acetate, N-vinylpyrrolidone, tetrahydrofurfuryl methacrylate, polystyrene macromonomer, and polymethyl methacrylate macromonomer. In addition, as other monomers, N-phenylmaleimide, N-cyclohexylmaleimide, and the like which are N-substituted maleimide monomers described in JP1998-300922A (JP-H10-300922A) can be used. These other monomers copolymerizable with a (meth)acrylic acid may be used singly, or two or more types thereof may be used.

As the alkali-soluble resin, benzyl (meth)acrylate/(meth)acrylic acid copolymers, benzyl (meth)acrylate/(meth)acrylic acid/2-hydroxyethyl (meth)acrylate copolymers, and multicomponent copolymers consisting of benzyl (meth)acrylate/(meth)acrylic acid/other monomers can be preferably used. In addition, 2-hydroxypropyl (meth)acrylate/polystyrene macromonomer/benzyl methacrylate/methacrylic acid copolymers, 2-hydroxy-3-phenoxypropyl acrylate/polymethyl methacrylate macromonomer/benzyl methacrylate/methacrylic acid copolymers, 2-hydroxyethyl methacrylate/polystyrene macromonomer/methyl methacrylate/methacrylic acid copolymers, 2-hydroxyethyl methacrylate/polystyrene macromonomer/benzyl methacrylate/methacrylic acid copolymers, and the like which are obtained by copolymerizing a 2-hydroxyethyl (meth)acrylate and described in JP1995-140654A (JP-H7-140654A) can also be preferably used.

The alkali-soluble resin preferably includes a polymer (a) obtained by polymerizing a monomer component including at least one of a compound represented by the following Formula (ED1) or a compound represented by the following Formula (ED2) (hereinafter, these compounds may be referred to as "ether dimer").

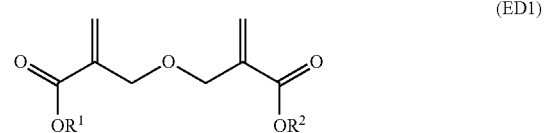

(ED1)

In Formula (ED1), $R^1$ and $R^2$ each independently represent a hydrocarbon group having 1 to 25 carbon atoms which may have a hydrogen atom or a substituent.

(ED2)

In Formula (ED2), R represents a hydrogen atom or an organic group having 1 to 30 carbon atoms. Regarding specific examples of Formula (ED2), the description in JP2010-168539A can be referred to.

In Formula (ED1), the hydrocarbon group having 1 to 25 carbon atoms which may have a substituent, represented by $R^1$ and $R^2$, is not particularly limited, and examples thereof include linear or branched alkyl groups such as methyl, ethyl, n-propyl, isopropyl, n-butyl, isobutyl, tert-butyl, tert-amyl, stearyl, lauryl, and 2-ethylhexyl; aryl groups such as phenyl; alicyclic groups such as cyclohexyl, tert-butylcyclohexyl, dicyclopentadienyl, tricyclodecanyl, isobornyl, adamantyl, and 2-methyl-2-adamantyl; alkyl groups substituted with alkoxy such as 1-methoxyethyl and 1-ethoxyethyl; and alkyl groups substituted with an aryl group such as benzyl. Among these, particularly, a substituent of a primary or secondary carbon that hardly separates due to an acid or heat, such as methyl, ethyl, cyclohexyl, or benzyl is preferable in view of heat resistance.

Regarding specific examples of the ether dimer, for example, paragraph 0317 of JP2013-29760A can be referred to, and the contents thereof are incorporated into this specification. The ether dimer may be used singly, or two or more types thereof may be used.

The alkali-soluble resin may include a constituent unit derived from a compound represented by the following Formula (X).

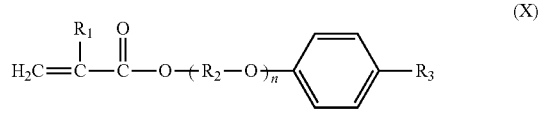

(X)

In Formula (X), $R_1$ represents a hydrogen atom or a methyl group. $R_2$ represents an alkylene group having 2 to 10 carbon atoms. $R_3$ represents a hydrogen atom or an alkyl group having 1 to 20 carbon atoms which may include a benzene ring. n represents an integer of 1 to 15.

In the above Formula (X), the number of carbon atoms of the alkylene group of $R_2$ is preferably 2 or 3. The number of carbon atoms of the alkyl group of $R_3$ is 1 to 20, and is preferably 1 to 10. The alkyl group of $R_3$ may include a benzene ring. Examples of the alkyl group represented by $R_3$ which includes a benzene ring include a benzyl group and a 2-phenyl(iso)propyl group.

Regarding the alkali-soluble resin, the description in paragraphs 0558 to 0571 of JP2012-208494A ([0685] to [0700] of US2012/0235099A corresponding thereto) and the description in paragraphs 0076 to 0099 of JP2012-198408A can be referred to, and the contents thereof are incorporated into this specification.

The acid value of the alkali-soluble resin is preferably 30 to 200 mgKOH/g. The lower limit thereof is more preferably not less than 50 mgKOH/g, and even more preferably not less than 70 mgKOH/g. The upper limit thereof is more preferably not greater than 150 mgKOH/g, and even more preferably not greater than 120 mgKOH/g.

In addition, the resin may have a polymerizable group. In a case where the resin has a polymerizable group, it is possible to form a hard film without using a curable compound to be described later.

Examples of the polymerizable group include a (meth) allyl group and a (meth)acryloyl group. Examples of the resin containing a polymerizable group include DIANAL NR series (manufactured by Mitsubishi Rayon Co., Ltd.), Photomer 6173 (COOH-containing polyurethane acrylic oligomer, manufactured by Diamond Shamrock Co., Ltd.), VISCOAT R-264, KS RESIST 106 (all manufactured by OSAKA ORGANIC CHEMICAL INDUSTRY LTD.), CYCLOMER P series (for example, ACA230AA), PLACCEL CF 200 series (all manufactured by Daicel Chemical Industries, Ltd.), Ebecryl 3800 (manufactured by Daicel-UCB Co., Ltd.), and ACRYCURE RD-F8 (manufactured by NIPPON SHOKUBAI CO., LTD.). The above-described epoxy resins are also be included.

In the near-infrared absorption composition according to the invention, the content of the resin is preferably 1 to 80 mass % with respect to the total solid content of the near-infrared absorption composition. The lower limit thereof is more preferably not less than 5 mass %, and even more preferably not less than 7 mass %. The upper limit thereof is more preferably not greater than 50 mass %, and even more preferably not greater than 30 mass %.

<<Curable Compound>>

The near-infrared absorption composition according to the invention may contain a curable compound. As the curable compound, a compound (hereinafter, may be referred to as "polymerizable compound) having a polymerizable group is preferable.

Examples of the polymerizable compound include a compound including a group having an ethylenically unsaturated bond, a cyclic ether (epoxy or oxetane) group, a methylol group, or the like, and a compound including a group having an ethylenically unsaturated bond is preferable. Examples of the group having an ethylenically unsaturated bond include a vinyl group, a (meth)allyl group, and a (meth)acryloyl group.

The polymerizable compound may be monofunctional or polyfunctional, and is preferably polyfunctional. In a case where a polyfunctional compound is included, near-infrared shieldability and heat resistance can be further improved. The number of functional groups is not particularly limited, but the compound is preferably bi- to octa-functional, and more preferably tri- to hexa-functional.

The polymerizable compound may have any chemical form such as a monomer, a prepolymer, an oligomer or a mixture thereof, or a polymer thereof. The polymerizable compound is preferably a monomer.

The polymerizable compound is preferably a tri- to pentadeca-functional (meth)acrylate compound, and more preferably a tri- to hexa-functional (meth)acrylate compound.

The curable compound is preferably a compound including a group having an ethylenically unsaturated bond.

Regarding examples of the compound including a group having an ethylenically unsaturated bond, the description in paragraphs 0033 and 0034 of JP2013-253224A can be referred to, and the contents thereof are incorporated into this specification.

Specific preferable examples thereof include ethyleneoxy-modified pentaerythritol tetraacrylate (as a commercially available product, NK ester ATM-35E; manufactured by Shin-Nakamura Chemical Co., Ltd.), dipentaerythritol triacrylate (as a commercially available product, KAYARAD D-330; manufactured by Nippon Kayaku Co., Ltd.), dipentaerythritol tetraacrylate (as a commercially available product, KAYARAD D-320; manufactured by Nippon Kayaku Co., Ltd.), dipentaerythritol penta(meth)acrylate (as a commercially available product, KAYARAD D-310; manufactured by Nippon Kayaku Co., Ltd.), dipentaerythritol hexa(meth)acrylate (as commercially available products, KAYARAD DPHA; manufactured by Nippon Kayaku Co., Ltd., A-DPH-12E; manufactured by Shin-Nakamura Chemical Co., Ltd.), and compounds including a structure in which these (meth)acryloyl groups are bonded via an ethylene glycol or a propylene glycol residue. In addition, oligomer types thereof can also be used.

In addition, the description of the polymerizable compound in paragraphs 0034 to 0038 of JP2013-253224A can be referred to, and the contents thereof are incorporated into this specification.

In addition, polymerizable monomers described in paragraph 0477 of JP2012-208494A ([0585] of US2012/0235099A corresponding thereto) are also included as specific examples, and the contents thereof are incorporated into this specification.

As the compound including a group having an ethylenically unsaturated bond, diglycerine ethyleneoxide (EO)-modified (meth)acrylate (as a commercially available product, M-460; manufactured by Toagosei Co., Ltd.) is preferable. Pentaerythritol tetraacrylate (manufactured by Shin-Nakamura Chemical Co., Ltd., A-TMMT) and 1,6-hexanediol diacrylate (manufactured by Nippon Kayaku Co., Ltd., KAYARAD HDDA) are also preferable. Oligomer types thereof can also be used. Examples thereof include RP-1040 (manufactured by Nippon Kayaku Co., Ltd.).

The compound including a group having an ethylenically unsaturated bond may further have an acid group such as a carboxy group, a sulfonate group, and a phosphate group.

Examples of the compound having an acid group include an ester of an aliphatic polyhydroxy compound with an unsaturated carboxylic acid. A polyfunctional monomer allowed to have an acid group by reacting a non-aromatic carboxylic acid anhydride with an unreacted hydroxy group of an aliphatic polyhydroxy compound is preferable. Particularly preferably, an aliphatic polyhydroxy compound is at least one of pentaerythritol or dipentaerythritol. Examples of commercially available products thereof include M-305, M-510, and M-520 of ARONIX series, as polybasic acid-modified acrylic oligomers manufactured by Toagosei Co., Ltd.

The acid value of the compound having an acid group is preferably 0.1 to 40 mgKOH/g. The lower limit thereof is more preferably not less than 5 mgKOH/g. The upper limit thereof is more preferably not greater than 30 mgKOH/g.

As an aspect of the curable compound, a compound having a caprolactone structure is also preferable.

Regarding the compound having a caprolactone structure, the description in paragraphs 0042 to 0045 of JP2013-253224A can be referred to, and the contents thereof are incorporated into this specification.

Examples of commercially available products thereof include SR-494 which is a tetrafunctional acrylate having four ethyleneoxy chains manufactured by Sartomer Inc., DPCA-60 which is a hexafunctional acrylate having six pentyleneoxy chains manufactured by Nippon Kayaku Co., Ltd., and TPA-330 which is a trifunctional acrylate having three isobutyleneoxy chains.

In a case where the near-infrared absorption composition according to the invention contains a curable compound, the content of the curable compound is preferably 1 to 90 mass % with respect to the total solid content of the near-infrared absorption composition. The lower limit thereof is more preferably not less than 15 mass %, and even more preferably not less than 40 mass %. The upper limit thereof is preferably not greater than 80 mass %, and even more preferably not greater than 75 mass %.

The curable compound may be used singly, or two or more types thereof may be used. In a case where two or more types are used, the total amount thereof is preferably within the above-described range.

<<Photopolymerization Initiator>>

The near-infrared absorption composition according to the invention may contain a photopolymerization initiator.

The content of the photopolymerization initiator is preferably 0.01 to 30 mass % with respect to the total solid content of the near-infrared absorption composition. The lower limit thereof is more preferably not less than 0.1 mass %, and even more preferably not less than 0.5 mass %. The upper limit thereof is more preferably not greater than 20 mass %, and even more preferably not greater than 15 mass %.

The photopolymerization initiator may be used singly, or two or more types thereof may be used. In a case where two or more types are used, the total amount thereof is preferably within the above-described range.

The photopolymerization initiator is not particularly limited, as long as it has a capability of initiating polymerization of the curable compound by light. The photopolymerization initiator can be appropriately selected according to the purpose. A photopolymerization initiator having photosensitivity to light rays from an ultraviolet region to a visible region is preferable.

The photopolymerization initiator is preferably a compound having an aromatic group, and examples thereof include an acylphosphine compound, an acetophenone-based compound, an α-aminoketone compound, a benzophenone-based compound, a benzoin ether-based compound, a ketal derivative compound, a thioxanthone compound, an oxime compound, a hexaarylbiimidazole compound, a trihalomethyl compound, an azo compound, an organic peroxide, an onium salt compound such as a diazonium compound, an iodonium compound, a sulfonium compound, an azinium compound, a benzoin ether-based compound, a ketal derivative compound, and a metallocene compound, an organic boron salt compound, a disulfone compound, and a thiol compound.

Regarding the photopolymerization initiator, the description in paragraphs 0217 to 0228 of JP2013-253224A can be referred to, and the contents thereof are incorporated into this specification.

As the oxime compound, IRGACURE-OXE01, IRGACURE-OXE02 (all manufactured by BASF SE), TR-PBG-304 (manufactured by Changzhou Tronly New Electronic Materials CO., LTD.), ADEKA ARKLS NCI-831, and ADEKA ARKLS NCI-930 (all manufactured by ADEKA Corporation), and the like which are commercially available products can be used.

As the acetophenone-based compound, IRGACURE-907, IRGACURE-369, and IRGACURE-379 (all manufactured by BASF SE) which are commercially available products can be used. As the acylphosphine compound, IRGACURE-819 and DAROCUR-TPO (all manufactured by BASF SE) which are commercially available products can be used.

According to the invention, an oxime compound having a fluorine atom can also be used as the photopolymerization initiator. Specific examples of the oxime compound having a fluorine atom include compounds described in JP2010-262028A, Compounds 24, and 36 to 40 described in JP2014-500852A, and Compound (C-3) described in JP2013-164471A. The contents thereof are incorporated into this specification.

<<Solvent>>

The near-infrared absorption composition according to the invention may contain a solvent. The solvent is not particularly limited, and can be appropriately selected according to the purpose, as long as respective components of the near-infrared absorption composition according to the invention can be evenly dissolved or dispersed. For example, water or an organic solvent can be used, and an organic solvent is preferable.

Preferable examples of the organic solvent include alcohols (for example, methanol), ketones, esters, aromatic hydrocarbons, halogenated hydrocarbons, dimethylformamide, dimethylacetamide, dimethylsulfoxide, and sulfolane. These may be used singly, or two or more types thereof may be used in combination. In a case where two or more types of solvents are used in combination, a mixed solution formed of two or more selected from methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, ethylene glycol monobutyl ether acetate, propylene glycol monomethyl ether, and propylene glycol monomethyl ether acetate is preferable.

Specific examples of the alcohols, the aromatic hydrocarbons, and the halogenated hydrocarbons include those described in paragraph 0136 of JP2012-194534A, and the contents thereof are incorporated into this specification. In addition, specific examples of the esters, the ketones, and the ethers include those described in paragraph 0497 of JP2012-208494A ([0609] of US2012/0235099A corresponding thereto), and further include n-amyl acetate, ethyl propionate, dimethyl phthalate, ethyl benzoate, methyl sulfate, acetone, methyl isobutyl ketone, diethyl ether, and ethylene glycol monobutyl ether acetate.

The amount of the solvent in the near-infrared absorption composition according to the invention is preferably an amount provided such that a solid content of the compound represented by Formula (1) is 10 to 90 mass %. The lower limit thereof is more preferably not less than 20 mass %. The upper limit thereof is more preferably not greater than 80 mass %.

<<Surfactant>>

The near-infrared absorption composition according to the invention may contain a surfactant. The surfactant may be used singly, or two or more types thereof may be used in combination. The content of the surfactant is preferably 0.0001 to 5 mass % with respect to the total solid content of the near-infrared absorption composition according to the invention. The lower limit thereof is more preferably not less than 0.005 mass %, and even more preferably not less than 0.01 mass %. The upper limit thereof is more preferably not greater than 2 mass %, and even more preferably not greater than 1 mass %.

As the surfactant, various surfactants such as a fluorine-based surfactant, a nonionic surfactant, a cation-based surfactant, an anion-based surfactant, and a silicone-based surfactant can be used. The near-infrared absorption composition according to the invention preferably contains at least one of a fluorine-based surfactant or a silicone-based surfactant. Due to the surfactant, the interface tension between a coating surface and a coating liquid is lowered, and wettability to the coating surface is thus improved. Therefore, liquid characteristics (particularly, fluidity) of the composition is improved, and uniformity of a coating thickness and liquid saving properties are further improved. As a result, even in a case where a film having a small thickness of approximately several micrometers is formed with a small amount of a liquid, a film having a uniform thickness with little thickness unevenness can be formed.

The fluorine content of the fluorine-based surfactant is preferably 3 to 40 mass %. The lower limit thereof is more preferably not less than 5 mass %, and even more preferably not less than 7 mass %. The upper limit thereof is more preferably not greater than 30 mass %, and even more preferably not greater than 25 mass %. A fluorine-based surfactant having a fluorine content within the above-described range is effective in view of uniformity of a thickness of a coating film and liquid saving properties, and satisfactory solubility is obtained.

Specific examples of the fluorine-based surfactant include surfactants described in paragraphs 0060 to 0064 of JP2014-41318A (paragraphs 0060 to 0064 of WO2014/17669A corresponding thereto), and the contents thereof are incorporated into this specification. Examples of commercially available products of the fluorine-based surfactant include MEGAFAC F-171, MEGAFAC F-172, MEGAFAC F-173, MEGAFAC F-176, MEGAFAC F-177, MEGAFAC F-141, MEGAFAC F-142, MEGAFAC F-143, MEGAFAC F-144, MEGAFAC R30, MEGAFAC F-437, MEGAFAC F-475, MEGAFAC F-479, MEGAFAC F-482, MEGAFAC F-554, MEGAFAC F-780, (all manufactured by DIC Corporation), FLUORAD FC430, FLUORAD FC431, FLUORAD FC171 (all manufactured by Sumitomo 3M Limited.), SURFLON S-382, SURFLON SC-101, SURFLON SC-103, SURFLON SC-104, SURFLON SC-105, SURFLON SC-1068, SURFLON SC-381, SURFLON SC-383, SURFLON S-393, and SURFLON KH-40 (all manufactured by Asahi Glass Co., Ltd.).

The following compound is also exemplified as the fluorine-based surfactant which is used in the invention.

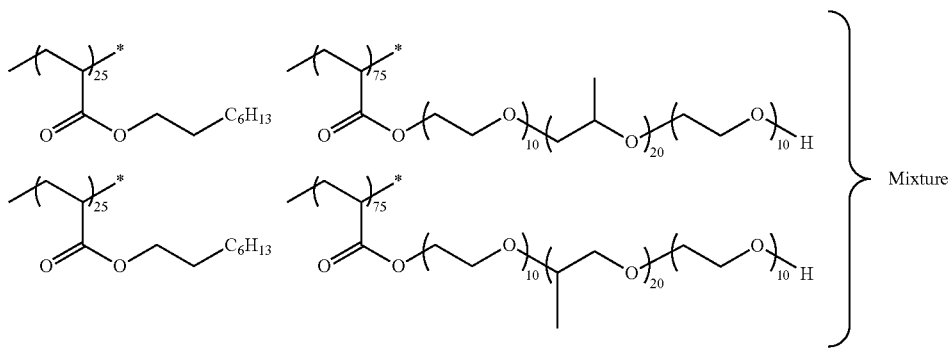

The weight average molecular weight of the above compound is, for example, 14,000.

Specific examples of the nonionic surfactant include nonionic surfactants described in paragraph 0553 of JP2012-208494A ([0679] of US2012/0235099A corresponding thereto), and the contents thereof are incorporated into this specification.

Specific examples of the cationic surfactant include cationic surfactants described in paragraph 0554 of JP2012-208494A ([0680] of US2012/0235099A corresponding thereto), and the contents thereof are incorporated into this specification.

Specific examples of the anionic surfactant include W004, W005, and W017 (manufactured by Yusho Co., Ltd.).

Examples of the silicone-based surfactant include silicone-based surfactants described in paragraph 0556 of JP2012-208494A ([0682] of US2012/0235099A corresponding thereto), and the contents thereof are incorporated into this specification.

<<Polymerization Inhibitor>>

The near-infrared absorption composition according to the invention may contain a small amount of a polymerization inhibitor in order to prevent unnecessary reaction of the curable compound during the manufacturing or preservation.

Examples of the polymerization inhibitor include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol), and N-nitrosophenylhydroxyamine cerous salt, and p-methoxyphenol is preferable.

In a case where the near-infrared absorption composition according to the invention contains a polymerization inhibitor, the content of the polymerization inhibitor is preferably 0.01 to 5 mass % with respect to the total solid content of the near-infrared absorption composition according to the invention.

<<Ultraviolet Absorbing Agent>>

The near-infrared absorption composition according to the invention may contain an ultraviolet absorbing agent.

The ultraviolet absorbing agent is a compound in which the light absorption coefficient per gram at a wavelength of 365 nm is greater than 100 and the light absorption coefficient per gram at a wavelength of 400 nm or greater is 10 or less. The light absorption coefficient is a value which is measured at a concentration of 0.01 g/L using an ethyl acetate solvent with an ultraviolet visible light spectrophotometer (manufactured by Varian, Cary-5 spectrophotometer).

As the ultraviolet absorbing agent, compounds in paragraphs 0137 to 0142 of JP2012-068418A (paragraphs 0251 to 0254 of US2012/0068292A corresponding thereto) can be used, and the contents thereof can be employed and are incorporated into this specification. Examples of commercially available products thereof include UV503 (DAITO CHEMICAL CO., LTD.).

The near-infrared absorption composition according to the invention may include or may not include an ultraviolet absorbing agent. However, in a case where the near-infrared absorption composition according to the invention includes an ultraviolet absorbing agent, the content of the ultraviolet absorbing agent is preferably 0.01 to 10 mass %, and more preferably 0.01 to 5 mass % with respect to the total solid content of the composition.

According to the invention, the ultraviolet absorbing agent may be used singly, or two or more types thereof may be used in combination.

<<Other Near-Infrared Absorption Substances>>

The near-infrared absorption composition according to the invention may further include a near-infrared absorption substance (hereinafter, also referred to as other near-infrared absorption substances) having a maximum absorption wavelength in a near-infrared region different from the maximum absorption wavelength of the compound represented by Formula (1). According to this aspect, it is possible to obtain a near-infrared cut filter which can absorb light in a near-infrared region with a wider wavelength region than in a case of light absorbed only by the compound represented by Formula (1).

Examples of other near-infrared absorption substances include a copper compound, a cyanine-based compound, a phthalocyanine-based compound, an iminium-based compound, a thiol complex-based compound, a transition metal oxide-based compound, a squarylium-based compound, a naphthalocyanine-based compound, a quaterrylene-based compound, a dithiolmetal complex-based compound, and a croconium-based compound.

As the phthalocyanine-based compound, the naphthalocyanine-based compound, the iminium-based compound, the cyanine-based compound, the squarylium-based compound, and the croconium-based compound, compounds described in paragraphs 0010 to 0081 of JP2010-111750A may be used, and the contents thereof are incorporated into this specification. Regarding the cyanine-based compound, for example, "Functional Dye, written by Okawara Shin, Matsuoka Ken, Kitao Teijirou, and Hirashima Kousuke, published by Kodansha Scientific Ltd." can be referred to, and the contents thereof are incorporated into this specification.

As the copper compound, copper compounds described in paragraphs 0013 to 0056 of JP2014-41318A and paragraphs 0012 to 0030 of JP2014-32380A may be used, and the contents thereof are incorporated into this specification.

Compounds disclosed in paragraphs 0004 to 0016 of JP1995-164729A (JP-H07-164729A), compounds disclosed in paragraphs 0027 to 0062 of JP2002-146254A, and near-infrared absorption particles which are disclosed in paragraphs 0034 to 0067 of JP2011-164583A, consist of crystallites of an oxide including at least one of Cu or P, and have a number average aggregate particle diameter of 5 to 200 nm may be used, and the contents thereof are incorporated into this specification.

In addition, as commercially available products thereof, "IRA842" manufactured by Exciton, "FD-25" manufactured by Yamada Kagaku Co., Ltd., and the like can be used.

In a case where other near-infrared absorption substances are contained, the content of other near-infrared absorption substances is preferably 0.01 to 50 mass %, and more preferably 0.01 to 45 mass % with respect to the total solid content of the composition according to the invention. According to the invention, other near-infrared absorption substances may be used singly, or two or more types thereof may be used in combination.

<<Other Components>>

Examples of other components which can be used in combination in the near-infrared absorption composition according to the invention include a sensitizing agent, a crosslinking agent, a curing accelerator, a filler, a thermal curing accelerator, a thermal polymerization inhibitor, and a plasticizer, and an adhesion promoter to a substrate surface and other auxiliary agents (for example, conductive particles, a filler, an antifoaming agent, a flame retardant, a leveling agent, a peeling promoter, an antioxidant, a fragrance material, a surface tension adjuster, and a chain transfer agent) may be used in combination.

In a case where these components are appropriately contained, it is possible to adjust desired characteristics such as stability and film properties of a near-infrared cut filter.

Regarding these components, for example, the description in paragraphs 0183 to 0228 of JP2012-003225A ([0237] to [0309] of US2013/0034812A corresponding thereto), paragraphs 0101 to 0104 and 0107 to 0109 of JP2008-250074A, paragraphs 0159 to 0184 of JP2013-195480A, and the like can be referred to, and the contents thereof are incorporated into this specification.

<Preparation and Use of Composition>

The near-infrared absorption composition according to the invention can be prepared by mixing the above-described components.

In the preparation of the composition, the components constituting the composition may be collectively formulated, or sequentially formulated after being dissolved or dispersed in an organic solvent. An input order or a work condition during the formulation is not particularly limited.

According to the invention, for the purpose of removing foreign substances, reducing defects, or the like, the composition is preferably filtrated with a filter. The filter can be used without limitation, as long as it has been used for the filtration use. Examples thereof include filters made of a fluorine resin such as polytetrafluoroethylene (PTFE), a polyamide resin such as nylon-6 or nylon-6,6, or a polyolefin resin (with high density and ultrahigh molecular weight) such as polyethylene or polypropylene (PP). Among these materials, polypropylene (including high-density polypropylene) and nylon are preferable.

The hole diameter of the filter is preferably 0.1 to 7.0 μm, more preferably 0.2 to 2.5 μm, even more preferably about 0.2 to 1.5 μm, and still more preferably 0.3 to 0.7 μm. In a case where the hole diameter is within this range, it is possible to securely remove fine foreign substances such as impurities or aggregates included in the composition, while the filter clogging is suppressed.

When the filter is used, a different filter may be combined therewith. In this case, the filtering in a first filter may be performed once, or twice or more times. In a case where the filtering is performed twice or more times by combining a different filter, the hole diameters of a second filter or thereafter are preferably equal to or greater than a hole diameter of a first filter. In addition, a first filter having a different hole diameter within the above-described range may be combined. Regarding the hole diameters herein, nominal values of filter manufacturers can be referred to. A commercially available filter can be selected from various filters provided by, for example, Nihon Pall Ltd., Toyo Roshi Kaisha, Ltd., Entegris Japan Co., Ltd. (formerly, Mykrolis Corporation), or Kitz Microfilter Corporation.

As a second filter, a filter formed with the same material as the above-described first filter can be used. The hole diameter of the second filter is preferably 0.2 to 10.0 μm, more preferably 0.2 to 7.0 μm, and even more preferably 0.3 to 6.0 μm. In a case where the hole diameter is within this range, foreign substances can be removed while component particles contained in the composition remain.

The viscosity of the near-infrared absorption composition according to the invention is preferably in the range of 1 to 3,000 mPa·s in a case where, for example, the near-infrared cut filter is formed by coating. The lower limit thereof is more preferably not less than 10 mPa·s, and even more preferably not less than 100 mPa·s. The upper limit thereof is more preferably not greater than 2,000 mPa·s, and even more preferably not greater than 1,500 mPa·s.

The near-infrared absorption composition according to the invention can also be used in a near-infrared cut filter (for example, a near-infrared cut filter for a wafer level lens) on a light receiving side of a solid-state imaging device, a near-infrared cut filter on a back surface side (a side opposite to a light receiving side) of a solid-state imaging device, and the like. In addition, the near-infrared absorption composition according to the invention may be directly applied to an image sensor to form a coating film.

Since the near-infrared absorption composition according to the invention can be supplied in a coatable state, a near-infrared cut filter can be easily formed on a desired member or a desired position in a solid-state imaging device.

The near-infrared absorption composition according to the invention can be used in, for example, (i) a near-infrared cut filter which can absorb light in a specific near-infrared region, (ii) a near-infrared cut filter which can absorb light in a near-infrared region with a wider wavelength region than in a case of light absorbed only by the compound represented by Formula (1), and the like.

In a case where the near-infrared absorption composition is used in the (i) near-infrared cut filter described above, it is preferable that the near-infrared absorption composition according to the invention contains the compound represented by Formula (1) and does substantially not contain a near-infrared absorption substance having a maximum absorption wavelength in a near-infrared region different from the maximum absorption wavelength of the compound represented by Formula (1). Here, the expression, substantially not contain means that the content of the substance is 1 mass % or less of the compound represented by Formula (1).

In a case where the near-infrared absorption composition is used in the (ii) near-infrared cut filter described above, it is preferable that the near-infrared absorption composition according to the invention contains an infrared absorption substance having a maximum absorption wavelength in a near-infrared region different from the maximum absorption wavelength of the compound represented by Formula (1), in addition to the compound represented by Formula (1).

<Cured Film and Near-Infrared Cut Filter>

A cured film and a near-infrared cut filter according to the invention use the above-described near-infrared absorption composition according to the invention.

Regarding the near-infrared cut filter according to the invention, light transmittance preferably satisfies at least one of the following Condition (1), Condition (2), Condition (3), or Condition (4), and more preferably satisfies all of Conditions (1) to (4).

(1) The light transmittance at a wavelength of 400 nm is preferably not less than 70%, more preferably not less than 80%, even more preferably not less than 85%, and particularly preferably not less than 90%.

(2) The light transmittance at a wavelength of 500 nm is preferably not less than 70%, more preferably not less than 80%, even more preferably not less than 90%, and particularly preferably not less than 95%.

(3) The light transmittance at a wavelength of 600 nm is preferably not less than 70%, more preferably not less than 80%, even more preferably not less than 90%, and particularly preferably not less than 95%.

(4) The light transmittance at a wavelength of 650 nm is preferably not less than 70%, more preferably not less than 80%, even more preferably not less than 90%, and particularly preferably not less than 95%.

The film thickness of the near-infrared cut filter according to the invention can be appropriately selected according to the purpose. The film thickness is preferably not greater than 300 μm, more preferably not greater than 200 μm, and even more preferably not greater than 100 μm. The lower limit of the film thickness is preferably not less than 0.1 μm, more preferably not less than 0.2 μm, and even more preferably not less than 0.3 μm.

Regarding the near-infrared cut filter according to the invention, light transmittance in a total wavelength range of 400 to 650 nm is preferably not less than 70%, more preferably not less than 80%, even more preferably not less than 90% in a film thickness of 200 µm or less. In addition, light transmittance at least one point in a wavelength range of 750 to 830 nm is preferably not greater than 20%, and more preferably not greater than 10%.

<Use of Near-Infrared Cut Filter>

The near-infrared cut filter according to the invention is used for lenses (camera lenses for digital cameras, cellular phones, vehicle-mounted cameras, and the like, and optical lenses such as f-θ lenses and pickup lenses) having a function of absorbing or cutting near infrared rays, optical filters for a semiconductor light receiving element, near-infrared absorbing films and near-infrared absorbing plates which shield heat rays for energy saving, agricultural coating agents for the purpose of selective use of sunlight, recording mediums which use near-infrared absorption heat, near-infrared cut filters for electronic devices or photos, protection glasses, sunglasses, heat ray shielding films, optical character reading/recording, prevention of copying of confidential documents, electrophotographic photoreceptors, laser welding, and the like. The near-infrared cut filter is also useful as a noise cut filter for a CCD camera and a filter for a CMOS image sensor.

<Method of Manufacturing Cured Film and Near-Infrared Cut Filter>

The cured film and the near-infrared cut filter according to the invention are obtained using the near-infrared absorption composition according to the invention. Specifically, these can be manufactured through a step of forming a film by applying the near-infrared absorption composition according to the invention to a support and a step of drying the film. The film thickness, lamination structure, and the like can be appropriately selected according to the purpose. In addition, a step of forming a pattern may be further performed.

The step of forming a film can be performed by applying the near-infrared absorption composition according to the invention to a support using a dropwise addition method (drop cast), a spin coater, a slit spin coater, a slit coater, screen printing, applicator coating, or the like. In a case of a dropwise addition method (drop cast), it is preferable to form a dropwise addition area of a composition having a photoresist as a partition wall on the support such that a uniform film can be obtained in a predetermined film thickness.

The support may be a transparent substrate consisting of glass or the like. The support may be a solid-state imaging device or another substrate provided on a light receiving side of the solid-state imaging device. In addition, the support may be a layer such as a planarizing layer provided on the light receiving side of the solid-state imaging device.

In the step of drying the film, the drying conditions vary depending on the respective components, type of the solvent, use ratio, and the like. For example, the drying is performed at a temperature of 60° C. to 150° C. for about 30 seconds to 15 minutes.

Examples of the step of forming a pattern include a method including a step of forming a film-shaped composition layer by applying the near-infrared absorption composition according to the invention to a support, a step of exposing the composition layer in a pattern shape, and a step of forming a pattern by developing and removing unexposed portions. As the step of forming a pattern, photolithography or a dry etching method may be used for forming a pattern.

The method of manufacturing a near-infrared cut filter may include other steps. The other steps are not particularly limited, and can be appropriately selected according to the purpose. Examples thereof include a step of treating a surface of a substrate, a pre-heating step (pre-baking step), a curing treatment step, and a post-heating step (post-baking step).

<<Pre-Heating Step and Post-Heating Step>>

The heating temperature in the pre-heating step and the post-heating step is preferably 80° C. to 200° C. The upper limit thereof is more preferably not higher than 150° C. The lower limit thereof is more preferably not lower than 90° C.

The heating time in the pre-heating step and the post-heating step is preferably 30 to 240 seconds. The upper limit thereof is more preferably not longer than 180 seconds. The lower limit thereof is more preferably not shorter than 60 seconds.

<<Curing Treatment Step>>

The curing treatment step is a step of performing a curing treatment on the formed film if necessary. In a case where this treatment is performed, the mechanical strength of the near-infrared cut filter is improved.

The curing treatment step is not particularly limited, and can be appropriately selected according to the purpose. Preferable examples thereof include an entire surface exposure treatment and an entire surface heating treatment. In the invention, the expression "exposure" includes not only irradiation of light having various wavelengths, but also irradiation of radiation such as electron rays and X-rays.

The exposure is preferably performed by radiation irradiation, and as the radiation which can be used in the exposure, particularly, electron rays, KrF, ArF, ultraviolet rays such as g-rays, h-rays, and i-rays, and visible light are preferably used.

Examples of the exposure method include stepper exposure and exposure using a high-pressure mercury lamp.

The exposure amount is preferably 5 to 3,000 mJ/cm$^2$. The upper limit thereof is more preferably not greater than 2,000 mJ/cm$^2$, and even more preferably not greater than 1,000 mJ/cm$^2$. The lower limit thereof is more preferably not less than 10 mJ/cm$^2$, and even more preferably not less than 50 mJ/cm$^2$.

Examples of the entire surface exposure treatment include a method of exposing an entire surface of the formed film. In a case where the near-infrared absorption composition according to the invention contains a polymerizable compound, the entire surface exposure promotes the curing of polymerization components in the film, and thus the curing of the film further proceeds, and mechanical strength and durability are improved.

The device which performs the entire surface exposure is not particularly limited, and can be appropriately selected according to the purpose. Preferable examples thereof include an ultraviolet (UV) exposure machine such as an ultrahigh-pressure mercury lamp.

Examples of the method for the entire surface heating treatment include a method of heating the entire surface of the formed film. Through the entire surface heating, the film hardness of the pattern can be increased.

The heating temperature in the entire surface heating is preferably 100° C. to 260° C. The lower limit thereof is more preferably not lower than 120° C., and even more preferably not lower than 160° C. The upper limit thereof is more preferably not higher than 240° C., and even more preferably not higher than 220° C. In a case where the heating temperature is within the above-described range, a film having excellent hardness is easily obtained.

In the entire surface heating, the heating time is preferably 1 to 180 minutes. The lower limit thereof is more preferably not shorter than 3 minutes, and even more preferably not shorter than 5 minutes. The upper limit thereof is more preferably not longer than 120 minutes.

The device which performs the entire surface heating is not particularly limited, and can be appropriately selected among known devices according to the purpose. Examples thereof include a dry oven, a hot plate, and an infrared heater.

<Solid-State Imaging Device and Infrared Sensor>

A solid-state imaging device according to the invention includes a cured film obtained using the near-infrared absorption composition according to the invention.

An infrared sensor according to the invention includes a cured film obtained using the near-infrared absorption composition according to the invention.

Hereinafter, an embodiment of the infrared sensor according to the invention will be described using FIG. 1.

In an infrared sensor 100 illustrated in FIG. 1, a reference numeral 110 represents a solid-state imaging device.

An imaging area provided on the solid-state imaging device 110 has a near-infrared cut filter 111 and a color filter 112. The near-infrared cut filter 111 can be formed using, for example, the near-infrared absorption composition according to the invention.

Areas 114 are provided between infrared transmission filters 113 and the solid-state imaging device 110. Resin layers (for example, transparent resin layers) which can transmit light of a wavelength transmitting the infrared transmission filters 113 are disposed on the areas 114. In the embodiment illustrated in FIG. 1, the resin layers are disposed on the areas 114, but the infrared transmission filters 113 may be formed on the areas 114. That is, the infrared transmission filters 113 may be formed on the solid-state imaging device 110.

Microlenses 115 are disposed on an incidence ray (hv) side of the color filters 112 and the infrared transmission filters 113. A planarizing layer 116 is formed so as to cover the microlenses 115.

According to the embodiment illustrated in FIG. 1, the film thicknesses of the color filters 112 and the film thicknesses of the infrared transmission filters 113 are the same, but the film thicknesses may be different from each other.

According to the embodiment illustrated in FIG. 1, the color filters 112 are provided closer to the incidence ray (hv) side than the near-infrared cut filters 111, but the near-infrared cut filters 111 may be provided closer to the incidence ray (hv) side than the color filters 112 by changing the order of the near-infrared cut filters 111 and the color filters 112.

According to the embodiment illustrated in FIG. 1, the near-infrared cut filters 111 and the color filters 112 are laminated to be adjacent to each other, but both of the filters do not have to be adjacent to each other and other layers may be interposed therebetween.

<<Near-Infrared Cut Filter 111>>

Characteristics of the near-infrared cut filter 111 are selected according to an emission wavelength of an infrared light emitting diode (infrared LED) to be described later. For example, the near-infrared cut filter 111 can be formed using the above-described near-infrared absorption composition according to the invention.

<<Color Filter 112>>

The color filter 112 is not particularly limited, and color filters for pixel formation which have been known can be used. For example, the description in paragraphs 0214 to 0263 of JP2014-043556A can be referred to, and the contents thereof are incorporated into this specification.

<<Infrared Transmission Filter 113>>

Characteristics of the infrared transmission filter 113 are selected according to an emission wavelength of an infrared LED to be described later. For example, the following description will be given on the assumption that an emission wavelength of an infrared LED is 830 nm.

Regarding the infrared transmission filter 113, a maximum value of the light transmittance in a thickness direction of the film in a wavelength range of 400 to 650 nm is preferably not greater than 30%, more preferably not greater than 20%, even more preferably not greater than 10%, and particularly preferably not greater than 0.1%. The transmittance preferably satisfies the above-described condition in the entire wavelength range of 400 to 650 nm. A maximum value in the wavelength range of 400 to 650 nm is generally not less than 0.1%.

Regarding the infrared transmission filter 113, a minimum value of the light transmittance in a thickness direction of the film in a wavelength range of 800 nm or greater (preferably 800 to 1,300 nm) is preferably not less than 70%, more preferably not less than 80%, even more preferably not less than 90%, and particularly preferably not less than 99.9%. The transmittance preferably satisfies the above-described condition at a portion of the wavelength range of 800 nm or greater, and preferably satisfies the above-described condition at a wavelength corresponding to the emission wavelength of an infrared LED to be described later. The minimum value of the light transmittance in a wavelength range of 900 to 1,300 nm is generally not greater than 99.9%.

The film thickness is preferably not greater than 100 μm, more preferably not greater than 15 μm, even more preferably not greater than 5 μm, and particularly preferably not greater than 1 μm. The lower limit thereof is preferably 0.1 μm. In a case where the film thickness is within the above-described range, it is possible to obtain a film satisfying the above-described spectral characteristics.

The methods of measuring the spectral characteristics and the film thickness of the film are as follows.

The film thickness measurement is performed on a substrate after drying which has a film using a stylus type surface profile measuring device (DEKTAK150 manufactured by ULVAC Technologies, Inc.).

Regarding the spectral characteristics of the film, the transmittance is measured in a wavelength range of 300 to 1,300 nm using an ultraviolet-visible-near-infrared spectrophotometer (U-4100 manufactured by Hitachi High-Technologies Corporation).

The above-described light transmittance condition may be achieved through any means. However, for example, the above-described light transmittance condition can be preferably achieved by allowing the composition to contain a colorant and adjusting the type and the content of the colorant. Examples of the colorant include compounds having a maximum absorption wavelength in a wavelength range of 400 to 700 nm. The colorant may be a pigment or a dye. As the colorant, for example, colorants described in paragraphs 0019 to 0028 of JP2013-064998A may be used, and the contents thereof are incorporated into this specification.

The infrared transmission filter 113 can be produced using, for example, a composition (infrared transmitting composition) containing two or more colorants selected from a red colorant, a yellow colorant, a blue colorant, and a purple colorant.

The content of the pigment in the colorant is preferably 95 to 100 mass % with respect to the total amount of the colorant. The lower limit thereof is more preferably not less than 97 mass %, and even more preferably not less than 99 mass %.

As an aspect of the colorant, two or more colorants selected from a red colorant, a yellow colorant, a blue colorant, and a purple colorant are preferably contained, and a red colorant, a yellow colorant, a blue colorant, and a purple colorant are more preferably contained. As preferable specific examples thereof, Color Index (C.I.) Pigment Red 254, C.I. Pigment Yellow 139, C.I. Pigment Blue 15:6, and C.I. Pigment Violet 23 are preferably contained.

In a case where the colorant contained in the infrared transmitting composition is obtained by combining a red colorant, a yellow colorant, a blue colorant, and a purple colorant, it is preferable that a mass ratio of the red colorant is 0.2 to 0.5, a mass ratio of the yellow colorant is 0.1 to 0.2, a mass ratio of the blue colorant is 0.25 to 0.55, and a mass ratio of the purple colorant is 0.05 to 0.15 with respect to the total amount of the colorants. It is more preferable that a mass ratio of the red colorant is 0.3 to 0.4, a mass ratio of the yellow colorant is 0.1 to 0.2, a mass ratio of the blue colorant is 0.3 to 0.4, and a mass ratio of the purple colorant is 0.05 to 0.15 with respect to the total amount of the colorants.

Next, an image pickup device will be described as an example in which the infrared sensor according to the invention is applied. As the infrared sensor, a motion sensor, a proximity sensor, a gesture sensor, and the like exist.

Figure 2:
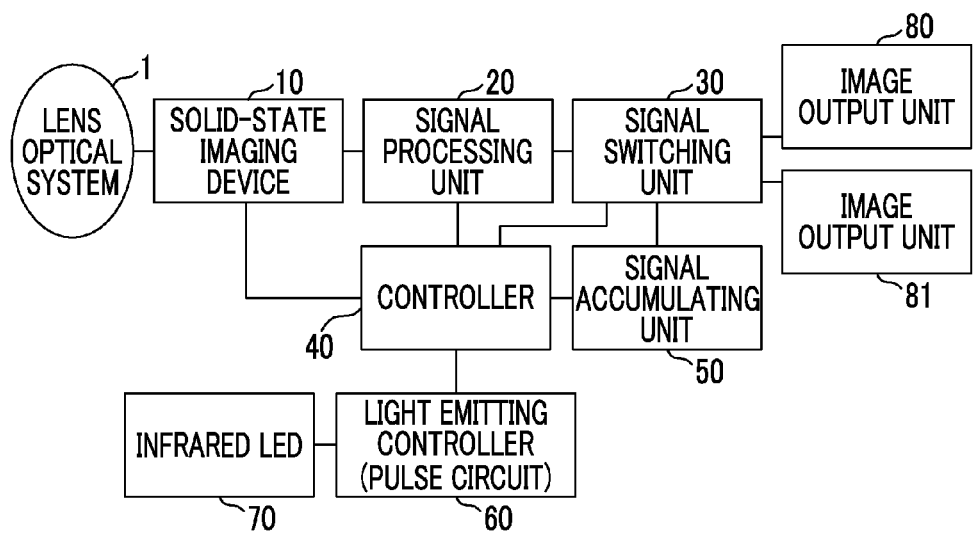
FIG. 2 is a block diagram illustrating functions of an image pickup device to which an infrared sensor according to the invention is applied.

FIG. 2 is a functional block diagram of an image pickup device. The image pickup device includes a lens optical system 1, a solid-state imaging device 10, a signal processing unit 20, a signal switching unit 30, a controller 40, a signal accumulating unit 50, a light emitting controller 60, an infrared LED 70 of a light emitting element which emits infrared light, and image output units 80 and 81. As the solid-state imaging device 10, the above-described infrared sensor 100 can be used. All or a portion of the configurations except for those of the solid-state imaging device 10 and the lens optical system 1 can be formed on the same semiconductor substrate. Regarding the respect configurations of the image pickup device, paragraphs 0032 to 0036 of JP2011-233983A can be referred to, and the contents thereof are incorporated into this specification.

A camera module having a solid-state imaging device and the above-described near-infrared cut filter can be incorporated into the image pickup device.

<Compound>

Next, a compound according to the invention will be described.

The compound according to the invention is a compound represented by Formula (1) described in the description of the near-infrared absorption composition according to the invention, and its preferable ranges are also similar to those in the description of the near-infrared absorption composition according to the invention.

The compound according to the invention has excellent solvent solubility. It also has excellent visible transparency and near-infrared shieldability.

In addition, by allowing the compound to have a group represented by Formula (W), film flexibility can be improved in the formation of a film. In addition, in a case where Formula (W) includes a long-chain alkyl structure, a compound having excellent solvent solubility and excellent moisture resistance can be made.

The compound according to the invention can be used in, for example, near-infrared cut filters for plasma display panels or solid-state imaging devices, or optical filters in heat ray shielding films, or as a photothermal conversion material in recordable optical disks or flash melt fixing materials. In addition, the compound according to the invention can be used as an information display material in security ink or invisible barcode ink.

EXAMPLES

Hereinafter, the invention will be described in further detail with reference to examples. Materials, amounts, ratios, process details, process orders, and the like provided in the following examples can be appropriately changed without departing from the gist of the invention. Accordingly, ranges of the invention are not limited to the following specific examples.

<Measurement of Weight Average Molecular Weight (Mw)>

The weight average molecular weight was measured through the following method.

Column Type: TSKgel Super HZ4000 (manufactured by TOSOH Corporation, 4.6 mm (internal diameter)×15 cm)
Developing Solvent: Tetrahydrofuran
Column Temperature: 40° C.
Flow Rate (sample amount injected): 60 μL
Device Name: High-Speed GPC (HLC-8220GPC) manufactured by TOSOH Corporation
Calibration Curve Base Resin: Polystyrene Synthesis Examples <Synthesis of Compound SQ-1>

Compound SQ-1 was synthesized by a method described in JP2011-208101A using Boronic Acid B-1 synthesized through the following synthesis route with reference to J. Mater. Chem., 2001, 11, 2801-2807.

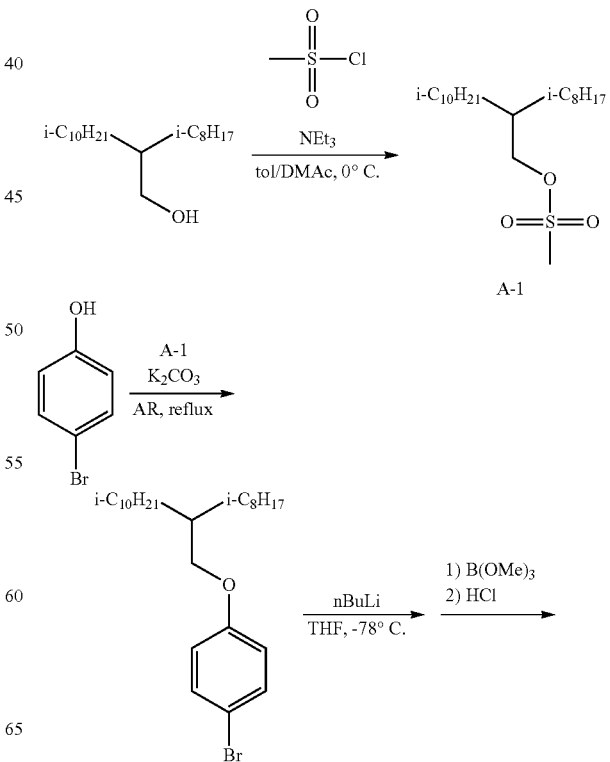

-continued

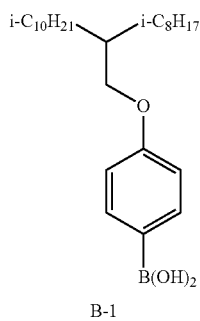

B-1

Identification Data of Compound SQ-1: MALDI TOF-MASS (flight time type mass spectrometry)
Calc. for [M+H]+: 1159.8, found: 1160.0.
<Synthesis of Compound SQ-2>
Compound SQ-2 was synthesized in the same manner as in the synthesis of Compound SQ-1 using Boronic Acid B-2 synthesized through the following synthesis route with reference to J. Am. Chem. Soc. 2001, 123, 11462-11467.

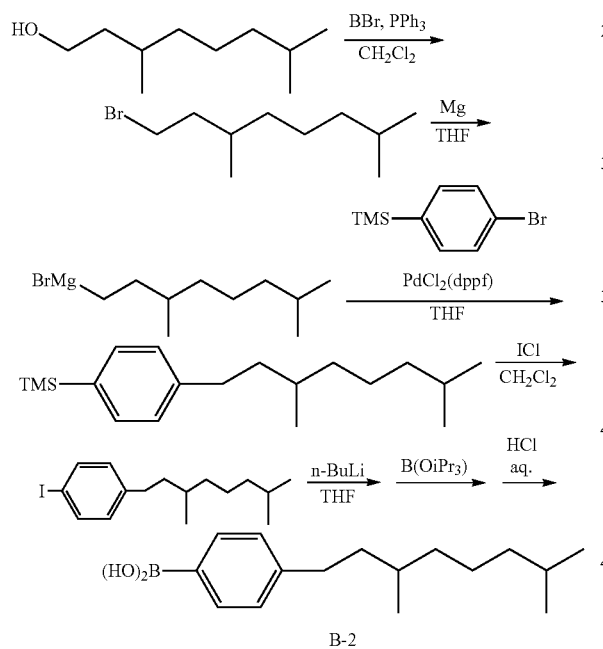

B-2

Identification Data of Compound SQ-2: MALDI TOF-MASS
Calc. for [M+H]+: 845.5, found: 845.8.
<Synthesis of Compound SQ-8>
Compound SQ-8 was synthesized in the same manner as in the synthesis of Compound SQ-1 using Boronic Acid B-3 synthesized in the same manner as in Tetrahedron, Volume 19, 1963, 821-826.

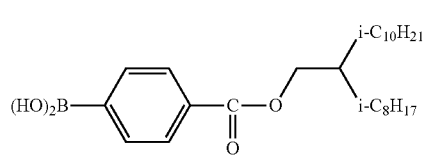

B-3

Identification Data of Compound SQ-8: MALDI TOF-MASS
Calc. for [M+H]+: 1215.8, found: 1216.0.
<Synthesis of Compound SQ-9>
Compound SQ-9 was synthesized in the same manner as in the synthesis of Compound SQ-1 using Boronic Acid B-4 synthesized through the following synthesis route with reference to Tetrahedron 68 (2012) 1192-1197.

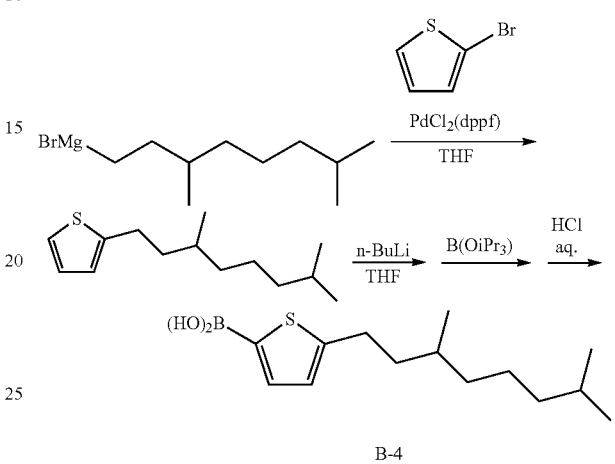

B-4

Identification Data of Compound SQ-9: MALDI TOF-MASS
Calc. for [M+H]+: 859.4, found: 859.6.
<Synthesis of Compound SQ-10>
Compound SQ-10 was synthesized in the same manner as in the synthesis of Compound SQ-9 using Boronic Acid B-5 synthesized through the following synthesis route which is substantially the same, except that 6-bromobenzothiophene was used in place of 2-bromothiophene in the synthesis of Compound SQ-9.

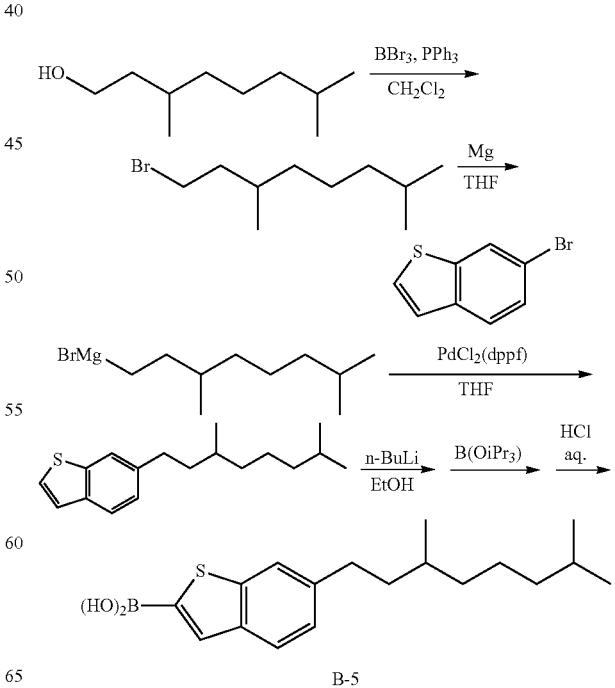

B-5

Identification Data of Compound Compound SQ-10: MALDI TOF-MASS

Calc. for [M+H]+: 959.5, found: 959.8.

<Synthesis of Compound SQ-3>

Compound SQ-3 was synthesized in the same manner as in the synthesis of Compound SQ-2, except that chiral alcohol was used as a starting material.

Identification Data of Compound SQ-3: MALDI TOF-MASS

Calc. for [M+H]+: 859.4, found: 859.6.

<Synthesis of Compound SQ-4>

Compound SQ-4 was synthesized in the same manner as in the synthesis of Compound SQ-1, except that 10-nonadecanol synthesized with reference to Dyes and Pigments 91 (2011) 182-191 was used as a starting material.

Identification Data of Compound SQ-4: MALDI TOF-MASS

Calc. for [M+H]+: 1131.8, found: 1132.0.

<Synthesis of Compound SQ-5>

Compound SQ-5 was synthesized in the same manner as in the synthesis of Compound SQ-1, except that diethylene glycol 2-brmoethyl methyl ether (manufactured by Tokyo Chemical Industry Co., Ltd.) was used in place of A-1.

Identification Data of Compound SQ-5: MALDI TOF-MASS

Calc. for [M+H]+: 891.4, found: 891.6.

<Synthesis of Compound SQ-6>

Compound SQ-6 was synthesized in the same manner, except that 1-bromodecane was used in place of A-1, and 2-bromophenol was used in place of 4-bromophenol in the synthesis of Compound SQ-1.

Identification Data of Compound SQ-6: MALDI TOF-MASS

Calc. for [M+H]+: 879.5, found: 879.7.

<Synthesis of Compound SQ-11>

Compound SQ-11 was synthesized in the same manner, except that 9-bromodecene was used in the synthesis of Compound SQ-6.

Identification Data of Compound SQ-11: MALDI TOF-MASS

Calc. for [M+H]+: 875.5, found: 875.7.

<Synthesis of Compound SQ-7>

Compound SQ-7 was synthesized in the same manner as in the synthesis of Compound SQ-1 using Boronic Acid B-6 synthesized with reference to Journal of Organic Chemistry, 2003, vol. 68, p. 3397 to 3405 with 10-nonadecanol as a starting material.

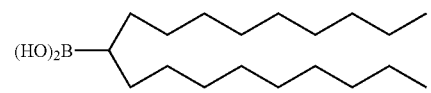

Identification Data of Compound SQ-7: MALDI TOF-MASS

Calc. for [M+H]+: 947.7, found: 948.0.

Compounds SQ-1 to SQ-11, R-1, and R-2: The following structures

SQ-1 to SQ-3 and SQ-8 to SQ-10 are compounds having asymmetric carbon. SQ-1, SQ-2, and SQ-8 to SQ-10 are racemic mixtures, and SQ-3 is an enantiomer simplex.

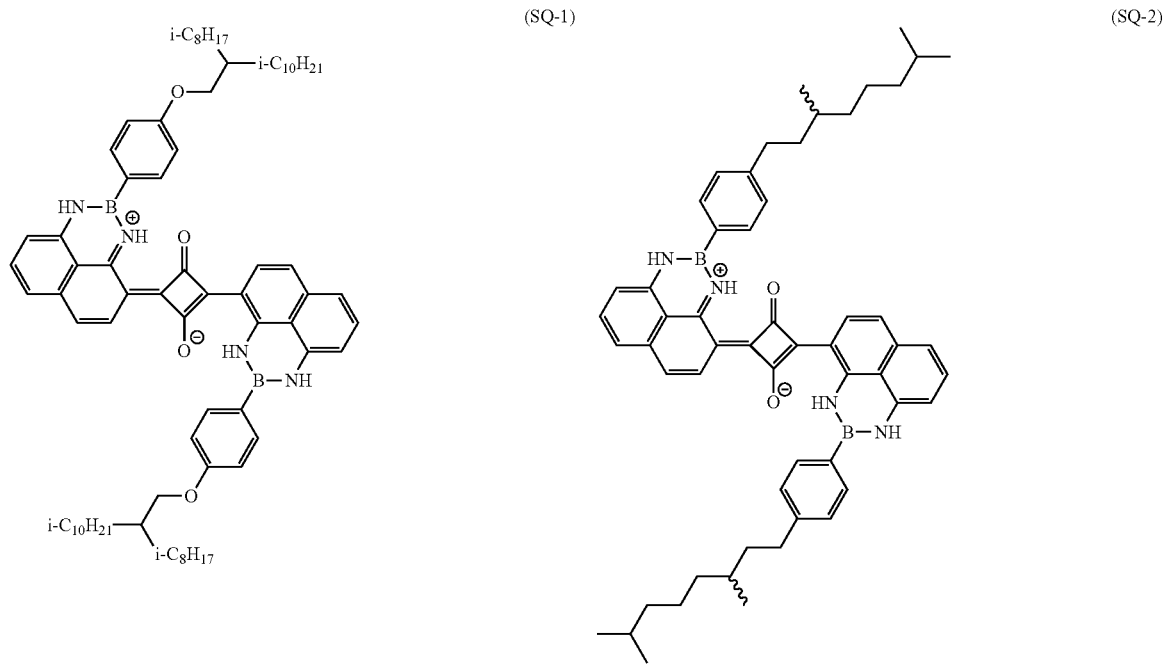

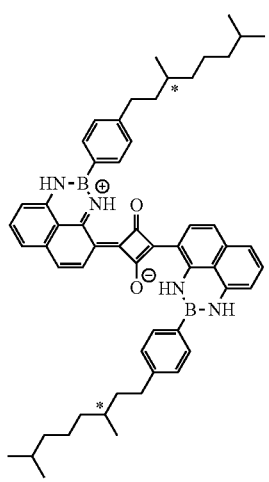
(SQ-3)
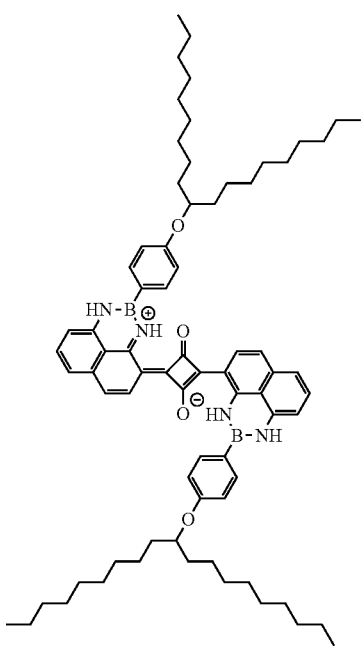
(SQ-4)
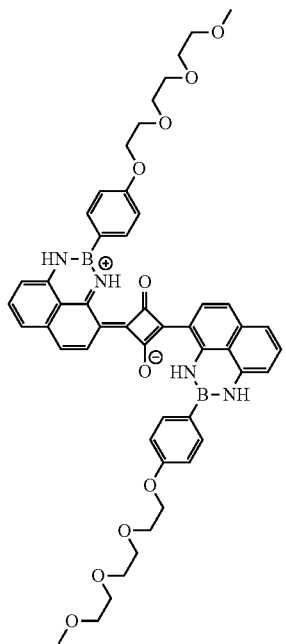
(SQ-5)

(SQ-6)
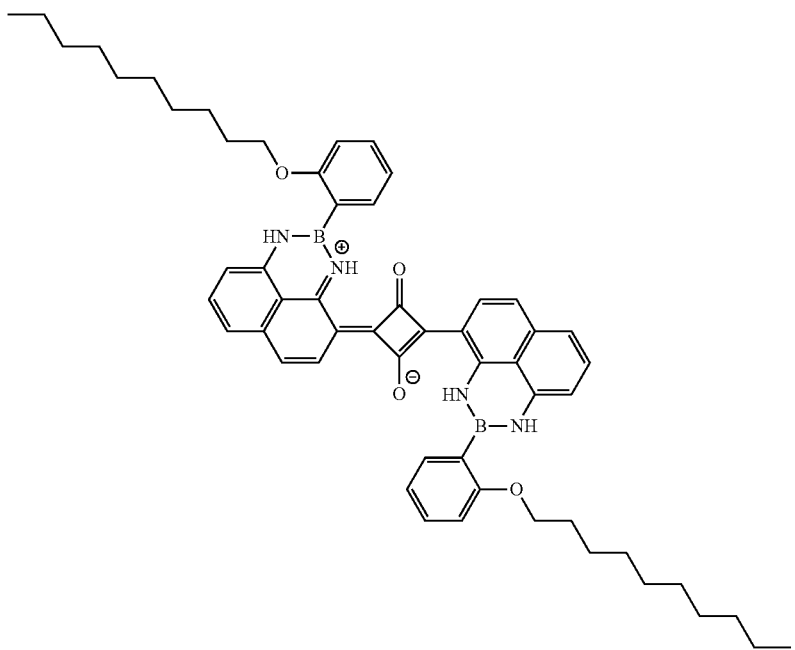
(SQ-7)
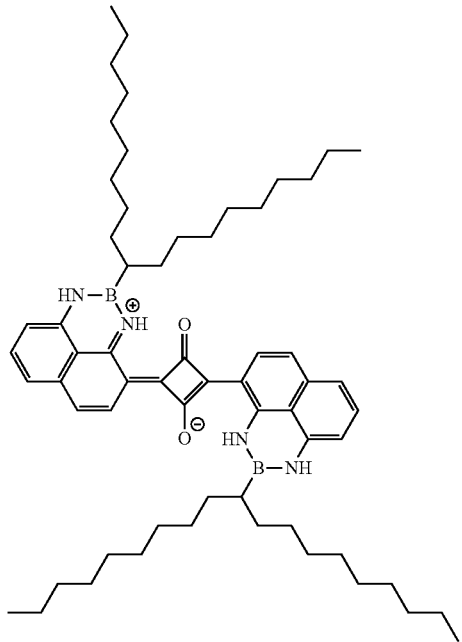
(SQ-8)
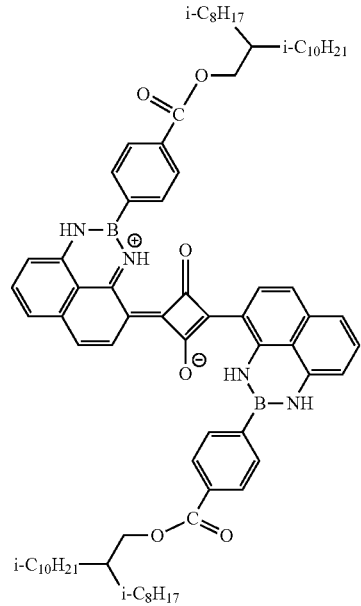

(SQ-9)
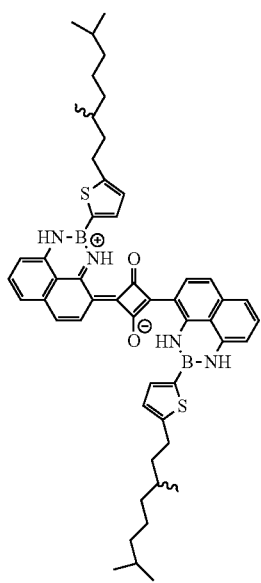
(SQ-10)
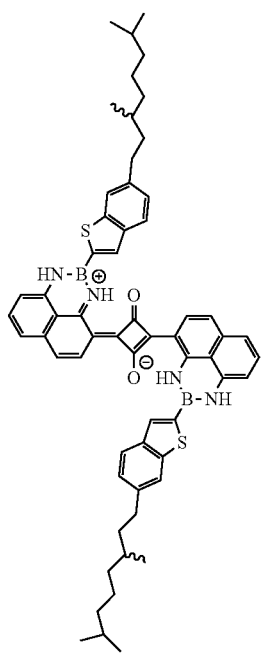
(SQ-11)
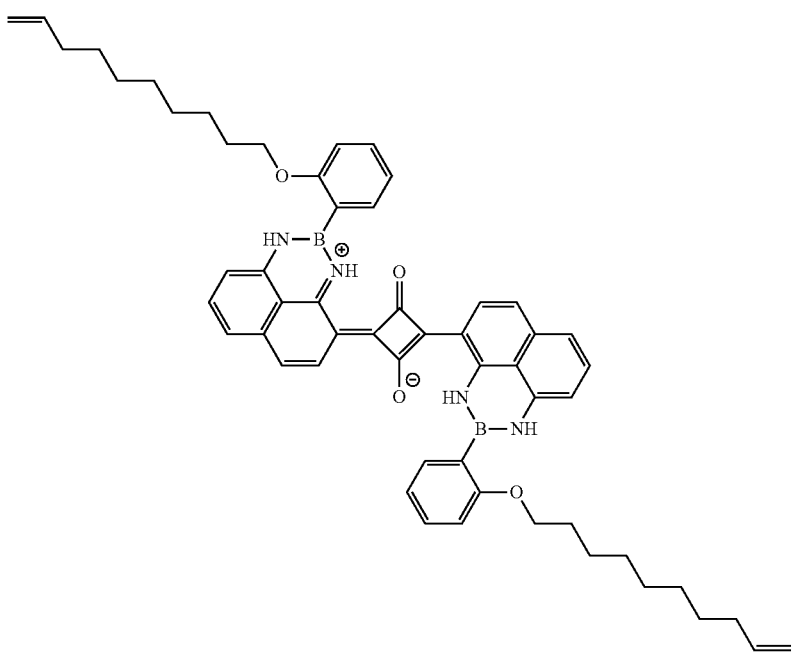

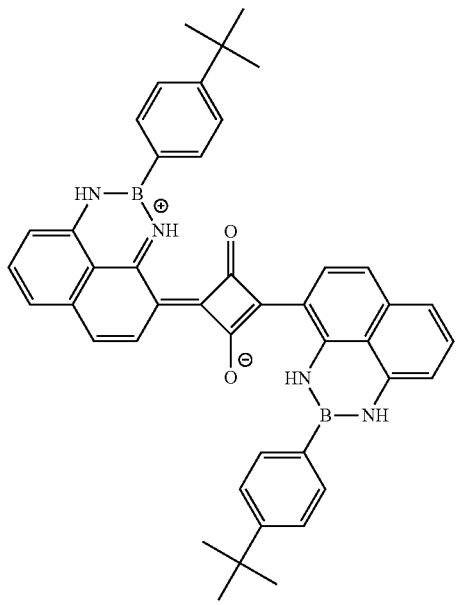

(R-1)

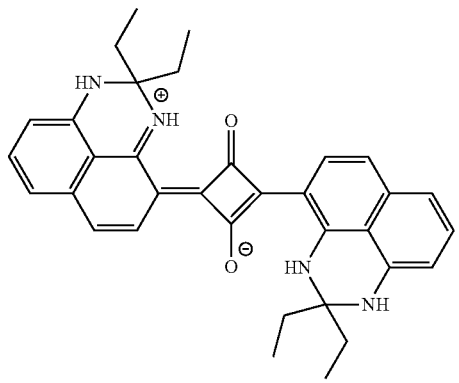

(R-2)

<Maximum Absorption Wavelength>

Each compound was dissolved in tetrahydrofuran to prepare a solution with a concentration of 1 g/L. Next, the absorption spectrum of the solution obtained by dissolving each compound was measured using UV-1800 manufactured by Shimadzu Corporation, and a maximum absorption wavelength (λmax) was measured. Maximum absorption wavelengths (λmax) of the compounds are shown in the following table.

<Solubility of Compound>

The solubility of each compound to each solvent (cyclohexanone, propylene glycol monomethyl ether acetate (PGMEA), and toluene) at 25° C. was evaluated based on the following standards.

A: The solubility of the compound to the solvent at 25° C. is 2 mass % or greater.

B: The solubility of the compound to the solvent at 25° C. is 1 mass % to less than 2 mass %.

C: The solubility of the compound to the solvent at 25° C. is 0.5 mass % to less than 1 mass %.

D: The solubility of the compound to the solvent at 25° C. is less than 0.5 mass %.

TABLE 1

| Compound | Maximum Absorption Wavelength | Solubility Cyclohexanone | PGMEA | Toluene |
|---|---|---|---|---|
| SQ-1 | 823 | A | A | A |
| SQ-2 | 823 | A | A | A |
| SQ-3 | 823 | B | A | A |
| SQ-4 | 823 | B | B | A |
| SQ-5 | 823 | B | A | B |
| SQ-6 | 828 | B | B | A |
| SQ-7 | 815 | B | B | B |
| SQ-8 | 842 | A | A | A |
| SQ-9 | 832 | A | B | A |
| SQ-10 | 840 | B | B | A |
| SQ-11 | 828 | A | B | A |
| R-1 | 827 | D | D | D |
| R-2 | 807 | C | C | B |

As shown in the above table, Compounds SQ-1 to SQ-11 had excellent solubility to each solvent. Compounds R-1 and R-2 did not have sufficient solubility.

<Preparation of Near-Infrared Absorption Composition>

A near-infrared absorption composition was prepared by mixing according to the following composition.

<Composition>

Compound shown in the following table: 2.3 parts

Resin 1 or Resin 2: 12.9 parts

Polymerizable compound: Dipentaerythritol hexaacrylate (manufactured by Nippon Kayaku Co., Ltd., product name KAYARAD DPHA): 12.9 parts Photopolymerization initiator: IRGACURE-OXE01 [2-(O-benzoyloxime)-1-[4-(phenylthio)phenyl]-1,2-octanedion], manufactured by BASF SE: 2.5 parts Ultraviolet absorbing agent: UV503 (DAITO CHEMICAL CO., LTD.): 0.5 parts Surfactant: The following mixture: 0.04 parts Polymerization inhibitor: Parametoxyphenol: 0.006 parts Cyclohexanone: 49.6 parts Propylene glycol monomethyl ether acetate: 19.3 parts Resin 1: Copolymer of benzyl methacrylate (BzMA) and methacrylic acid (MAA) (composition ratio (mass ratio): (BzMA/MAA)=(80/20), Mw=15,000)

Resin 2: Copolymer of allyl methacrylate (AMA) and methacrylic acid (MAA) (composition ratio (mass ratio): (AMA/MAA)=(80/20), Mw=15,000)

Surfactant: The following mixture (Mw=14,000)

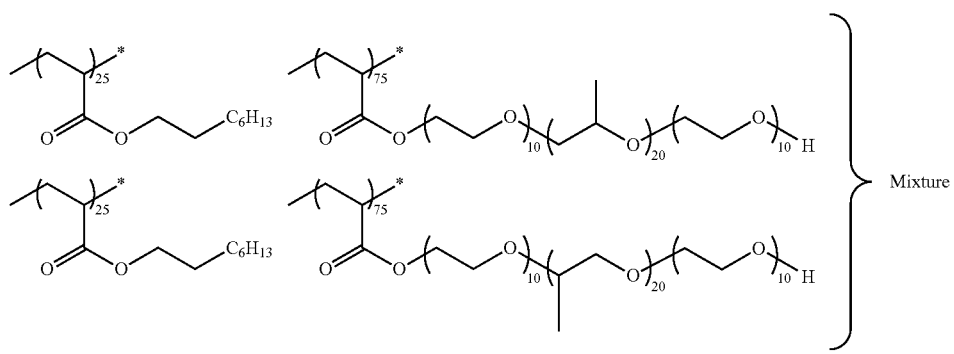

<Production of Cured Film>

Each composition was applied to a glass substrate (1737 manufactured by Corning Inc.) using a spin coater such that a film thickness after drying was 1.0 μm, and a heating treatment (pre-baking) was performed thereon for 120 seconds using a hot plate at 100° C.

Next, entire surface exposure was performed at 500 mJ/cm$^2$ using an i-ray stepper exposure device FPA-3000i5+ (manufactured by Canon Inc.). Next, paddle development was performed for 60 seconds at 23° C. using a developing machine (CD-2060, manufactured by FUJIFILM Electronics Materials Co., Ltd.), and a rinsing treatment was performed with pure water. Then, spray drying was performed thereon. Using a hot plate at 200° C., a heating treatment (post-baking) was performed for 300 seconds to obtain a cured film.

<Evaluation of Coating Film>

Each composition was applied to a glass substrate (1737 manufactured by Corning Inc.) using a spin coater such that a film thickness after drying was 1.0 μm, and the state of the coating film was visually observed.

A: There was compound precipitation.
B: There was no compound precipitation.

<Heat Resistance>

The obtained, cured film was heated for 5 minutes at 200° C., and then a value ΔEab of color difference before and after a heat resistance test was measured using a color meter MCPD-1000 (manufactured by Otsuka Electronics Co., Ltd.). A smaller value ΔEab indicates more satisfactory heat resistance.

The value ΔEab is a value obtained from the following color difference formula according to a CIE 1976 (L*, a*, b*) space color system (Handbook of Color Science, New Edition, edited by the Color Science Association of Japan, (1985), p. 266).

$$\Delta Eab = \{(\Delta L^*)^2 + (\Delta a^*)^2 + (\Delta b^*)^2\}^{1/2}$$

<<Determination Standards>>

A: Value ΔEab<3
B: 3≤Value ΔEab<5
C: 5≤Value ΔEab<10
D: 10≤Value ΔEab<20
E: 20≤Value ΔEab <Light Resistance>

The obtained, cured film was irradiated with 10,000 Lux of light using a Xe lamp for 10 hours through an ultraviolet cut filter. Then, a value ΔEab of color difference before and after a light resistance test was measured using a color meter MCPD-1000 (manufactured by Otsuka Electronics Co., Ltd.).

<<Determination Standards>>

A: Value ΔEab<3
B: 3≤Value ΔEab<5
C: 5≤Value ΔEab<10
D: 10≤Value ΔEab<20
E: 20≤Value ΔEab

TABLE 2

| | Compound | Resin | Coating Film | Heat Resistance | Light Resistance |
|---|---|---|---|---|---|
| Example 1 | SQ-1 | Resin 2 | A | A | A |
| Example 2 | SQ-2 | Resin 1 | A | A | A |
| Example 3 | SQ-3 | Resin 1 | A | A | A |
| Example 4 | SQ-4 | Resin 2 | A | A | A |
| Example 5 | SQ-5 | Resin 2 | A | B | A |
| Example 6 | SQ-6 | Resin 2 | A | A | A |
| Example 7 | SQ-7 | Resin 2 | A | B | B |
| Example 8 | SQ-8 | Resin 1 | A | A | A |
| Example 9 | SQ-9 | Resin 2 | A | A | A |
| Example 10 | SQ-10 | Resin 2 | A | A | A |
| Example 11 | SQ-11 | Resin 2 | A | A | A |
| Comparative Example 1 | R-1 | Resin 2 | B | B | B |
| Comparative Example 2 | R-2 | Resin 1 | B | C | D |

From the above results, in the examples using the compound according to the invention, the solubility of the compound was satisfactory, there was no compound precipitation in the coating film, and thus the properties of the coating film was satisfactory. Furthermore, the examples were excellent in heat resistance and light resistance.

However, in the comparative examples, the solubility of the compound was not sufficient, and compound precipitation was shown in the coating film.

In addition, in a case where bending stress was repeatedly applied to films formed by applying the near-infrared absorption compositions of the examples and the comparative examples to a polyethylene naphthalate film or a triacetyl cellulose film, cracks, film surface roughness, or peeling occurred in the comparative examples. However, in the examples, a state which was almost the same as the state before the application of stress was maintained.

EXPLANATION OF REFERENCES

1: lens optical system
10: solid-state imaging device
20: signal processing unit
30: signal switching unit
40: controller
50: signal accumulating unit
60: light emitting controller 70: infrared LED
80, 81: image output unit
100: infrared sensor
110: solid-state imaging device
111: near-infrared cut filter
112: color filter
113: infrared transmission filter
114: area
115: microlens
116: planarizing layer
hv: incidence ray

What is claimed is:

1. A near-infrared absorption composition comprising:
a compound represented by Formula (1); and
a resin,

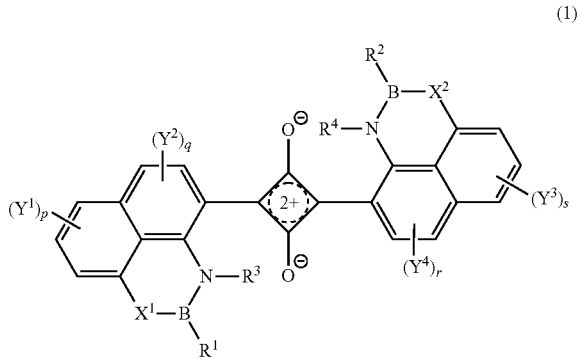

(1)

in the formula, $R^1$ and $R^2$ each independently represent an alkyl group, an alkenyl group, an aryl group, a heteroaryl group, or a group represented by Formula (W), and at least one of $R^1$ and $R^2$ represents a group represented by Formula (W), $R^3$ and $R^4$ each independently represent a hydrogen atom or an alkyl group, $X^1$ and $X^2$ each independently represent an oxygen atom or $-N(R^5)-$, $R^5$ represents a hydrogen atom, an alkyl group, an aryl group, or a heteroaryl group, $Y^1$ to $Y^4$ each independently represent a substituent, and each of $Y^1$ and $Y^2$, and $Y^3$ and $Y^4$ may be bonded to form a ring structure, in a case where the compound represented by Formula (1) has more than one of each of $Y^1$ to $Y^4$, these may be bonded to each other to form a ring structure, respectively, p and s each independently represent an integer of 0 to 3, and q and r each independently represent an integer of 0 to 2, and $$-S^1-L^1-T^1 \quad (W)$$

in Formula (W), $S^1$ represents a single bond, an arylene group, or a heteroarylene group, $L^1$ represents an alkylene group, an alkenylene group, an alkynylene group, $-O-$, $-S-$, $-NR^{L1}-$, $-CO-$, $-COO-$, $-OCO-$, $-CONR^{L1}-$, $-NR^{L1}CO-$, $-SO_2-$, $-OR^{L2}-$, or a group obtained by combining two or more thereof, $R^{L1}$ represents a hydrogen atom or an alkyl group, and $R^{L2}$ represents an alkylene group, $T^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group, in a case where $S^1$ is a single bond, $L^1$ is an alkylene group, and $T^1$ is an alkyl group, the total number of carbon atoms included in $L^1$ and $T^1$ is not less than 13, and in a case where $S^1$ is an arylene group, the total number of carbon atoms included in $L^1$ and $T^1$ is not less than 5.

2. The near-infrared absorption composition according to claim 1,
wherein in Formula (W), $S^1$ is an arylene group or a heteroarylene group.

3. The near-infrared absorption composition according to claim 1,
wherein in Formula (W), $L^1$ is an alkylene group, an alkenylene group, $-O-$, $-OR^{L2}-$, or a group obtained by combining two or more thereof, and $R^{L2}$ is an alkylene group.

4. The near-infrared absorption composition according to claim 1,
wherein in Formula (W), a $-L^1-T^1$ portion includes a branched alkyl structure.

5. The near-infrared absorption composition according to claim 1,
wherein in Formula (W), a $-L^1-T^1$ portion includes asymmetric carbon.

6. The near-infrared absorption composition according to claim 1,
wherein the compound represented by Formula (1) includes two or more types of optical isomers.

7. The near-infrared absorption composition according to claim 1,
wherein in Formula (1), $R^3$ and $R^4$ each independently represent a hydrogen atom or a methyl group.

8. The near-infrared absorption composition according to claim 1,
wherein in Formula (1), p, q, r, and s are 0.

9. The near-infrared absorption composition according to claim 1,
wherein in Formula (1), $X^1$ and $X^2$ are oxygen atoms.

10. The near-infrared absorption composition according to claim 1,
wherein in Formula (1), $X^1$ and $X^2$ each independently represent any one of the followings:

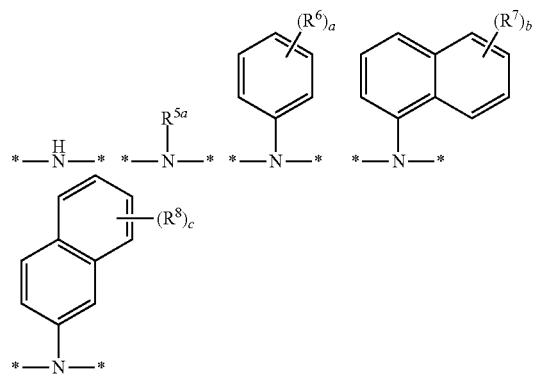

in the formula, $R^{5a}$ represents an alkyl group, $R^6$ to $R^8$ each independently represent a substituent, a represents an integer of 0 to 5, b and c each represent an integer of 0 to 7, and * represents a bond.

11. The near-infrared absorption composition according to claim 1, further comprising:
a solvent.

12. The near-infrared absorption composition according to claim 1, further comprising:
a curable compound.

13. A cured film which is prepared using the near-infrared absorption composition according to claim 1.

14. A near-infrared cut filter comprising:
the cured film according to claim 13.

15. A solid-state imaging device comprising:
the cured film according to claim 13.

16. An infrared sensor comprising:
the cured film according to claim 13.

17. A compound which is represented by Formula (1):

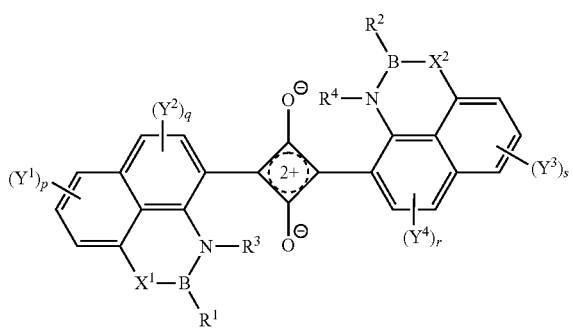

(1)

in the formula, $R^1$ and $R^2$ each independently represent an alkyl group, an alkenyl group, an aryl group, a heteroaryl group, or a group represented by Formula (W), and at least one of $R^1$ and $R^2$ represents a group represented by Formula (W), $R^3$ and $R^4$ each independently represent a hydrogen atom or an alkyl group, $X^1$ and $X^2$ each independently represent an oxygen atom or —N($R^5$)—, $R^5$ represents a hydrogen atom, an alkyl group, an aryl group, or a heteroaryl group, $Y^1$ to $Y^4$ each independently represent a substituent, and each of $Y^1$ and $Y^2$, and $Y^3$ and $Y^4$ may be bonded to form a ring structure, in a case where the compound represented by Formula (1) has more than one of each of $Y^1$ to $Y^4$, these may be bonded to each other to form a ring structure, respectively, p and s each independently represent an integer of 0 to 3, and q and r each independently represent an integer of 0 to 2, and $$—S^1-L^1-T^1 \quad (W)$$

in Formula (W), $S^1$ represents a single bond, an arylene group, or a heteroarylene group, $L^1$ represents an alkylene group, an alkenylene group, an alkynylene group, —O—, —S—, —$NR^{L1}$—, —CO—, —COO—, —OCO—, —$CONR^{L1}$—, —$NR^{L1}CO$—, —$SO_2$—, —$OR^{L2}$—, or a group obtained by combining two or more thereof, $R^{L1}$ represents a hydrogen atom or an alkyl group, and $R^{L2}$ represents an alkylene group, $T^1$ represents an alkyl group, a cyano group, a hydroxy group, a formyl group, a carboxy group, an amino group, a thiol group, a sulfo group, a phosphoryl group, a boryl group, a vinyl group, an ethynyl group, an aryl group, a heteroaryl group, a trialkylsilyl group, or a trialkoxysilyl group, in a case where $S^1$ is a single bond, $L^1$ is an alkylene group, and $T^1$ is an alkyl group, the total number of carbon atoms included in $L^1$ and $T^1$ is not less than 13, and in a case where $S^1$ is an arylene group, the total number of carbon atoms included in $L^1$ and $T^1$ is not less than 5.

* * * * *